United States Patent
Purandare et al.

(10) Patent No.: US 10,550,125 B2
(45) Date of Patent: Feb. 4, 2020

(54) PRODRUGS OF IMIDAZOTRIAZINE COMPOUNDS AS CK2 INHIBITORS

(71) Applicant: BRISTOL-MYERS SQUIBB COMPANY, Princeton, NJ (US)

(72) Inventors: Ashok Vinayak Purandare, Pennington, NJ (US); Kurt Zimmermann, Durham, CT (US); Honghe Wan, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/769,113

(22) PCT Filed: Oct. 19, 2016

(86) PCT No.: PCT/US2016/057580
§ 371 (c)(1),
(2) Date: Apr. 18, 2018

(87) PCT Pub. No.: WO2017/070135
PCT Pub. Date: Apr. 27, 2017

(65) Prior Publication Data
US 2018/0305364 A1    Oct. 25, 2018

Related U.S. Application Data

(60) Provisional application No. 62/243,808, filed on Oct. 20, 2015.

(51) Int. Cl.
| *A61K 31/53* | (2006.01) |
| *C07D 487/04* | (2006.01) |
| *A61P 19/02* | (2006.01) |
| *A61P 17/06* | (2006.01) |
| *A61P 35/02* | (2006.01) |

(52) U.S. Cl.
CPC ............ *C07D 487/04* (2013.01); *A61P 17/06* (2018.01); *A61P 19/02* (2018.01); *A61P 35/02* (2018.01)

(58) Field of Classification Search
CPC ............................ C07D 471/04; C07D 487/04
USPC .......................................................... 548/184
See application file for complete search history.

(56) References Cited

U.S. PATENT DOCUMENTS

| 7,331,539 | B2* | 2/2008 | Jara-Almonte | ........ E03C 1/2665 241/46.014 |
| 8,445,676 | B2* | 5/2013 | Purandare | ............ C07D 487/04 544/183 |
| 8,940,736 | B2* | 1/2015 | Purandare | ............... A61K 31/53 514/232.5 |
| 9,273,057 | B2* | 3/2016 | Purandare | ............... A61K 31/53 |
| 9,556,178 | B2* | 1/2017 | Purandare | ............... A61K 31/53 |
| 2007/0213300 | A1 | 9/2007 | Liu et al. | |

FOREIGN PATENT DOCUMENTS

WO    WO 2014/011974 A1    1/2014

\* cited by examiner

*Primary Examiner* — Samantha L Shterengarts
(74) *Attorney, Agent, or Firm* — Ellitt Korsen; Hong Liu

(57) ABSTRACT

The invention provides pharmaceutically active compounds of formula (I) and prodrugs thereof. The formula (I) 2-(aminophenylamino)-4-amino-7-cyano-imidazo[2,1-f][1,2,4]triazine derivatives inhibit CK2 protein kinase activity, thereby making them useful for treating cancer, psoriasis and rheumatoid arthritis.

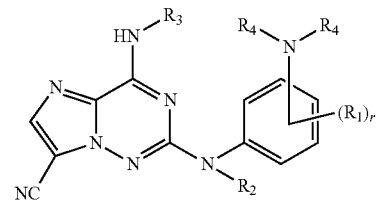

5 Claims, No Drawings

PRODRUGS OF IMIDAZOTRIAZINE COMPOUNDS AS CK2 INHIBITORS

CROSS-REFERENCE TO RELATED APPLICATIONS

This application claims priority from U.S. Provisional Application No. 62/243,808 filed Oct. 20, 2015, the disclosures of which are incorporated herein by reference in their entirety.

FIELD OF THE INVENTION

The invention relates to novel substituted imidazotriazine compounds and the prodrugs thereof useful as protein kinase inhibitors. The invention also relates to methods of using the compounds in the treatment of proliferative and other types of diseases and to pharmaceutical compositions containing the compounds.

BACKGROUND OF THE INVENTION

The invention relates to fused heterocyclic compounds which inhibit protein kinase enzymes, compositions which contain protein kinase inhibiting compounds and methods of using inhibitors of protein kinase enzymes to treat diseases which are characterized by an overexpression or upregulation of protein kinases. Protein kinases mediate intracellular signal transduction. They do this by affecting a phosphoryl transfer from a nucleoside triphosphate to a protein acceptor that is involved in a signaling pathway. There are a number of kinases and pathways through which extracellular and other stimuli cause a variety of cellular responses to occur inside the cell. An extracellular stimulus may affect one or more cellular responses related to cell growth, migration, differentiation, secretion of hormones, activation of transcription factors, muscle contraction, glucose metabolism, and control of protein synthesis and regulation of cell cycle.

Many diseases are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

Serine/threonine kinases are a class of protein kinases that are among the most promising drug targets for future small molecule inhibitors. Inhibition of serine/threonine kinases is likely to have relevance to the treatment of cancer, diabetes and a variety of inflammatory disorders. The successful development of GLEEVEC® as a Bcr/Abl protein kinase inhibitor has provided further evidence that protein kinases including protein kinase CK2 are valid drug targets for potential cancer therapies.

Protein kinase CK2 (formerly known as casein kinase II) is a highly conserved serine/threonine kinase. Protein kinase CK2 is ubiquitously distributed and constitutively active in eukaryotes. In mammals, the enzyme exists in two isozymic forms due to variations in the catalytic subunits of the enzyme. The CK2 holoenzyme is a heterotetrameric complex composed of two catalytic α (CK2A1) subunits or α' (CK2A2) subunits and two regulatory β-subunits. The formation of CK2 complexes containing the catalytic subunits requires dimerization of the regulatory β-subunits. CK2 interacts with a variety of cellular proteins and has been implicated in cell replication such as cell proliferation and differentiation, cellular survival, and tumorigenesis. With respect to tumorigenesis, protein kinase CK2 has been implicated in kidney tumors (Stalter et al., "Asymmetric expression of protein kinase CK2 subunits in human kidney tumors", *Biochem. Biophys. Res. Commun.*, 202:141-147 (1994)), mammary gland tumors (Landesman-Bollag et al., "Protein kinase CK2 in mammary gland tumorigenesis", *Oncology*, 20:3247-3257 (2001)), lung carcinoma (Daya-Makin et al., "Activation of a tumor-associated protein kinase (p40TAK) and casein kinase II in human squamous cell carcinomas and adenocarcinomas of the lung", *Cancer Res.*, 54:2262-2268 (1994)), head and neck carcinoma (Faust et al., "Antisense oligonucleotides against protein kinase CK2-α inhibit growth of squamous cell carcinoma of the head and neck in vitro", *Head Neck*, 22:341-346 (2000)), and prostate cancer (Wang et al., "Role of protein kinase CK2 in the regulation of tumor necrosis factor-related apoptosis inducing ligand-induced apoptosis in prostate cancer cells", *Cancer Res.*, 66:2242-2249 (2006)).

Inhibitors of protein kinases are widely sought and small molecule compounds capable of modulating protein kinases have been reported. For example, pyrazolotriazines as CK2 kinase inhibitors were reported by Nie et al. (*Bioorganic & Medicinal Chemistry Letters*, 17:4191-4195 (2007); 18:619-623 (2008)). In addition, certain imidazotriazine compounds and CK2 kinase inhibitors were disclosed in WO 2007/038314, published Apr. 5, 2007, US 2008/0045536, published Feb. 21, 2008, WO 2008/116064, published Sep. 25, 2008, WO 2010/042699, published Apr. 15, 2010, WO 2011/123493, published Oct. 6, 2011, WO 2014/011974, published Jan. 16, 2014, all assigned to the present assignee. The present invention relates to a new class of imidazotriazine-carbonitriles found to be effective inhibitors of protein kinases, particularly the CK2 kinase. These novel compounds are provided to be useful as pharmaceuticals with desirable stability, bioavailability, therapeutic index and toxicity values that are important to their drugability.

SUMMARY OF THE INVENTION

The invention is directed to fused heterocyclic compounds of Formula (I) or stereoisomers, tautomers, pharmaceutically acceptable salts, solvates thereof, which inhibit protein kinase enzymes, especially protein kinase CK2 for the treatment of cancer such as non-small cell lung cancer.

The present invention also provides processes and intermediates for making the compounds of the present invention or stereoisomers, tautomers, pharmaceutically acceptable salts, solvates thereof.

The present invention also provides pharmaceutical compositions comprising a pharmaceutically acceptable carrier and at least one of the compounds of the present invention or stereoisomers, tautomers, pharmaceutically acceptable salts, solvates thereof.

The present invention also provides methods for inhibiting the activity of protein kinase CK2 comprising administering to a host in need of such treatment a therapeutically effective amount of at least one of the compounds of the present invention or stereoisomers, tautomers, pharmaceutically acceptable salts, solvates thereof.

The present invention also provides methods for inhibiting angiogenesis or treating cancers comprising administering to a host in need of such treatment a therapeutically effective amount of at least one of the compounds of the present invention or stereoisomers, tautomers, pharmaceutically acceptable salts, solvates thereof.

The present invention also provides the compounds of the present invention or stereoisomers, tautomers, pharmaceutically acceptable salts, solvates thereof, for use in therapy.

The present invention also provides the use of the compounds of the present invention or stereoisomers, tautomers, pharmaceutically acceptable salts, solvates thereof, in preparing a medicament for the treatment of cancer in a human patient, particularly a cancer such as non-small cell lung cancer receptive to treatment via inhibition of the CK2 enzyme.

These and other features of the invention will be set forth in the expanded form as the disclosure continues.

DETAILED DESCRIPTION OF THE INVENTION

The invention provides for novel imidazotriazine compounds useful as therapeutic agents, pharmaceutical compositions employing such novel compounds and for methods of using such compounds.

In accordance with the invention, there are disclosed compounds of Formula (I) including enantiomers, diastereomers, tautomers, pharmaceutically-acceptable salts, hydrates, or solvates thereof,

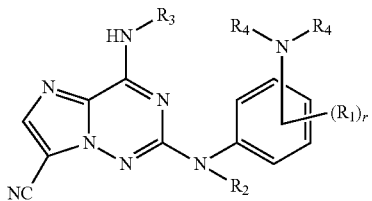

wherein
$R_1$ is H, halogen, CN, —NHC(O)$C_{1-4}$alkyl, —NHC(O)O$C_{1-4}$ alkyl, —CHF$_2$ or —OCHF$_2$
$R_2$ is H, —C(=O)O(CR$_c$R$_c$)$_r$OC(=O)R$_d$, —C(=O)N(CR$_c$R$_c$)$_r$OC(=O)R$_d$, or —C(=O)S(CR$_c$R$_c$)$_r$OC(=O)R$_d$;
$R_3$ is $C_{1-3}$alkyl or $C_{3-6}$ cycloalkyl;
$R_4$ and $R_4$ together with the nitrogen atom to which they are both attached form a 4- to 6-membered heterocycle containing carbon atoms and 0-3 additional heteroatoms selected from NR$_5$ O, and S, wherein the heterocycle is substituted with 1-3 R$_6$;
$R_5$ is —CHR$_c$OR$_b$, —CHR$_c$S(O)$_p$R$_c$, —CHR$_c$NR$_a$R$_a$, —CHR$_c$C(=O)NR$_a$R$_a$, —CHR$_c$C(=O)NR$_a$S(O)$_p$R$_c$, —CHR$_c$NHC(=O)OR$_b$, —CHR$_c$OC(=O)R$_d$, —CHR$_c$S(O)$_2$NR$_a$R$_a$, —CHR$_c$NR$_a$S(O)$_p$NR$_a$R$_a$, or —CHR$_c$NR$_a$S(O)$_p$R$_c$;
$R_6$ is H, halogen, —OR$_b$, —NR$_a$R$_a$, —NR$_a$C(=O)R$_b$, —NHC(=O)OR$_b$, or —(CR$_c$R$_c$)$_r$C(=O)NR$_a$R$_a$, or, —OC(=O)(CH$_2$)$_r$NH$_2$, and —NHS(O)$_2$($C_{1-4}$alkyl);
$R_a$, is H or $C_{1-6}$ alkyl;
$R_b$ is H or $C_{1-6}$ alkyl;
$R_c$ is H or $C_{1-6}$ alkyl;
$R_d$ is straight or branched, saturated or unsaturated alkyl, allyl, cycloalkyl, cyclohetероalkyl, aryl, arylalkyl, heteroaryl, or heteroarylalkyl, each optionally substituted;
r is zero, 1, 2 or 3;
provided when $R_2$ is H, then $R_4$ and $R_4$ together with the nitrogen atom to which they are both attached form

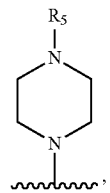

and $R_5$ is —CH(CH$_3$)C(=O)NR$_a$R$_a$.

In another aspect, there are disclosed compounds of Formula (I) including enantiomers, diastereomers, tautomers, pharmaceutically-acceptable salts, hydrates, or solvates thereof, wherein
$R_1$ is H, halogen, or CN;
$R_2$ is H or —C(=O)O(CR$_c$R$_c$)$_r$OC(=O)R$_d$;
$R_3$ is methyl, ethyl, or cyclopropyl;
$R_4$ and $R_4$ together with the nitrogen atom to which they are both attached form a 4- to 6-membered saturated monocyclic heterocycle containing carbon atoms and 0-1 NR$_5$, wherein the heterocycle is substituted with 1-3 R$_6$;
$R_5$ is —CHR$_c$OR$_b$, —CHR$_c$S(O)$_p$R$_c$, —CHR$_c$NR$_a$R$_a$, —CHR$_c$C(=O)NR$_a$R$_a$, —CHR$_c$C(=O)NR$_a$S(O)$_p$R$_c$, —CHR$_c$NHC(=O)OR$_b$, —CHR$_c$OC(=O)R$_d$, —CHR$_c$S(O)$_2$NR$_a$R$_a$, or —CHR$_c$NR$_a$S(O)$_p$R$_c$;
$R_6$ is H, —OR$_b$, —NHC(=O)OR$_b$, or —(CR$_c$R$_c$)$_r$C(=O)NR$_a$R$_a$;
$R_a$, is H or $C_{1-6}$ alkyl;
$R_b$ is H or $C_{1-6}$ alkyl;
$R_c$ is H or $C_{1-6}$ alkyl;
$R_d$ is straight or branched, saturated or unsaturated alkyl, allyl, cycloalkyl, cyclohetероalkyl, aryl, arylalkyl, heteroaryl, or heteroarylalkyl, each optionally substituted with $C_{1-2}$ alkyl, —C(O)OH, or —OP(O)(OH)$_2$; and
r is zero, 1, 2 or 3.

In another aspect, there are disclosed compounds of Formula (I) including enantiomers, diastereomers, tautomers, pharmaceutically-acceptable salts, hydrates, or solvates thereof, wherein
$R_1$ is H, Cl, or CN;
$R_2$ is —C(=O)O(CR$_c$R$_c$)$_r$OC(=O)R$_d$;
$R_3$ is ethyl or cyclopropyl;
$R_4$ and $R_4$ together with the nitrogen atom to which they are both attached form

$R_5$ is —CHR$_c$C(=O)NH$_2$;
$R_6$ is H;
$R_c$ is H or $C_{1-6}$ alkyl;
$R_d$ is

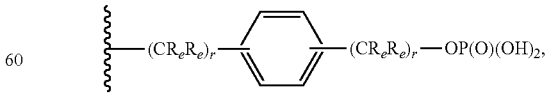

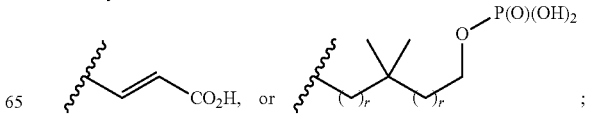

$R_e$ is H or $C_{1-4}$ alkyl; and r is zero, 1, 2 or 3.

In another aspect, there are disclosed compounds of Formula (I) including enantiomers, diastereomers, tautomers, pharmaceutically-acceptable salts, hydrates, or solvates thereof, wherein $R_1$ is H, Cl, or CN;

$R_2$ is —C(=O)OCH$_2$OC(=O)$R_d$;

$R_3$ is ethyl;

$R_4$ and $R_4$ together with the nitrogen atom to which they are both attached form

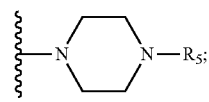

$R_5$ is —CH(CH$_3$)C(=O)NH$_2$;

$R_d$ is

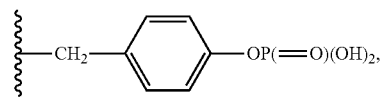

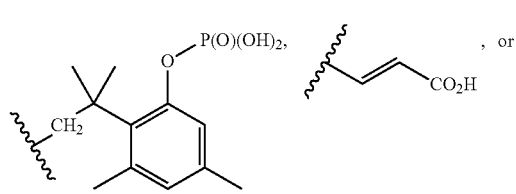

In another aspect, there is disclosed a compound from the group consisting of

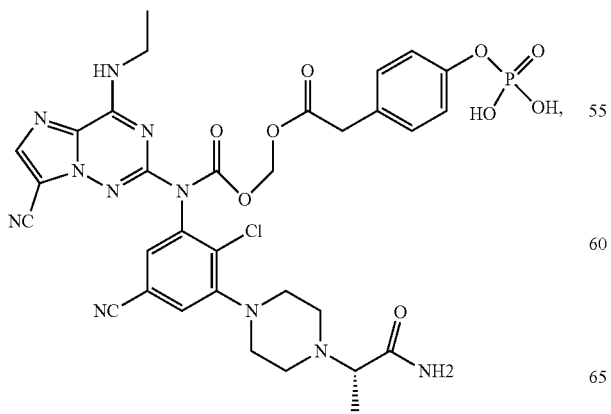

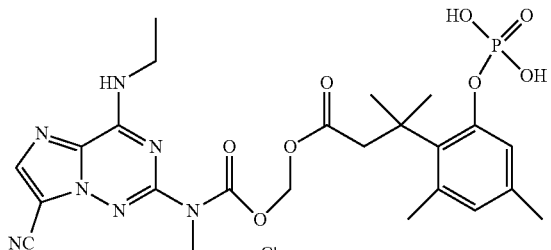

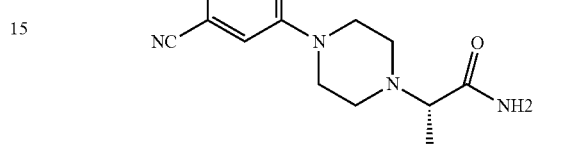

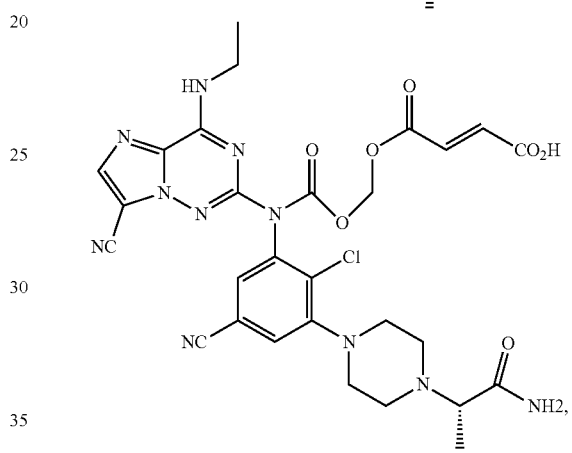

or a stereoisomer, a tautomer, a pharmaceutically acceptable salt thereof.

In another aspect, there is disclosed a compound having the structure

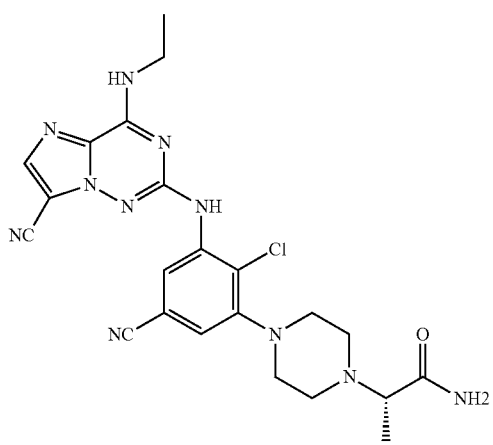 [SMILES: CCNc1nc(Nc2cc(C#N)cc(N3CCN([C@@H](C)C(N)=O)CC3)c2Cl)nn2c(C#N)cnc12]

or a stereoisomer, a tautomer, a pharmaceutically acceptable salt thereof.

It should further be understood that solvates (e.g., hydrates) of the compounds of Formula (I) are also within the scope of the invention. Methods of solvation are generally known in the art. The inventive compounds may either be in the free or hydrate form.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms.

The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials.

All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Definitions

The following are definitions of terms used in this specification and appended claims. The initial definition provided for a group or term herein applies to that group or term throughout the specification and claims, individually or as part of another group, unless otherwise indicated.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —CONH$_2$ is attached through the carbon atom.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

The term "halogen" or "halo" refers to fluorine (F), chlorine (Cl), bromine (Br) and iodine (I).

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

As used herein, "carbocycle," "carbocyclic residue," or "carbocyclyl" is intended to mean any stable 3-, 4-, 5-, 6-, or 7-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0] bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle," "carbocyclic residue," or "carbocyclyl" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

The term "aryl" refers to monocyclic, bicyclic, tricyclic aromatic hydrocarbon groups having 6 to 15 carbon atoms in the ring portion, such as phenyl, naphthyl, biphenyl and diphenyl groups, each of which may be substituted. Aryl groups which are bicyclic or tricyclic must include at least one fully aromatic ring but the other fused ring or rings may be aromatic or non-aromatic. When an aryl is substituted with a further heterocyclic ring, said ring may be attached to the aryl through a carbon atom or a heteroatom and said ring in turn is optionally substituted with one to two substituents as valence allows.

The terms "aryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy; a sulfinyl; a heteroaryl or substituted heteroaryl; an alkylthio; a carbonyl; an alkenyl; or an alkylsulfonyl, respectively.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

An "alkylidene" group refers to an alkylene group consisting of at least two carbon atoms and at least one carbon-carbon double bond. Substituents on this group include those in the definition of "substituted alkyl".

The term "cycloalkyl" refers to an optionally substituted, saturated cyclic hydrocarbon ring systems, preferably containing 1 to 3 rings and 3 to 7 carbons per ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

As used herein, the term "heterocycle," "heterocyclyl," "heterocyclic ring" or "heterocyclic group" is intended to mean a stable 4-, 5-, 6-, or 7-membered monocyclic or bicyclic or 7-, 8-, 9-, 10-, 11-, 12-, 13-, or 14-membered bicyclic heterocyclic ring which is saturated, partially unsaturated or fully unsaturated or aromatic, and which consists of carbon atoms and 1, 2, 3 or 4 heteroatoms independently selected from the group consisting of N, O and S; and including any bicyclic group in which any of the above-defined heterocyclic rings is fused to a benzene ring. The nitrogen and sulfur heteroatoms may optionally be oxidized (i.e., N→O and S(O)$_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle," "heterocyclyl," "heterocyclic ring" or "heterocyclic group" is used, it is intended to include heteroaryl.

Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from the group consisting of O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and $S(O)_p$) and the nitrogen atoms may optionally be quaternized.

Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, dihydroisoquinolinyl, tetrahydroquinolinyl, isoquinolinyl, benzimidazolyl, benzopyranyl, benzoxazinyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, and the like.

Exemplary tricyclic heteroaryl groups include carbazolyl, benzidolyl, phenanthrollinyl, acridinyl, phenanthridinyl, xanthenyl and the like.

The term "heteroatoms" shall include oxygen, sulfur and nitrogen.

As referred to herein, the term "substituted" means that one or more hydrogen atoms is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

The term "Prodrug" refers to a derivative of an active compound (drug) that undergoes a transformation under the conditions of use, such as within the body, to release an active drug. Prodrugs are frequently, but not necessarily, pharmacologically inactive until converted into the active drug. Prodrugs are typically obtained by masking a functional group in the drug believed to be in part required for activity with a prodrug group to form a promoiety which undergoes a transformation, such as cleavage, under the specified conditions of use to release the functional group, and hence the active drug. The cleavage of the promoiety may proceed spontaneously, such as by way of a hydrolysis reaction, or it may be catalyzed or induced by another agent, such as by an enzyme, by light, by acid, or by a change of or exposure to a physical or environmental parameter, such as a change of temperature, or combination thereof. The agent may be endogenous to the conditions of use, such as an enzyme present in the cells to which the prodrug is administered or the acidic conditions of the stomach, or it may be supplied exogenously.

When any variable occurs more than one time in any constituent or formula for a compound, its definition at each occurrence is independent of its definition at every other occurrence. Thus, for example, if a group is shown to be substituted with 1-3 $R_e$, then said group may optionally be substituted with up to three $R_e$ groups and $R_e$ at each occurrence is selected independently from the definition of $R_e$. Also, combinations of substituents and/or variables are permissible only if such combinations result in stable compounds.

When a dotted ring is used within a ring structure, this indicates that the ring structure may be saturated, partially saturated or unsaturated.

UTILITY

The compounds of the invention may be used to modulate kinase activities.

Applicants have discovered that compounds of Formula (I) have particular utility in treating proliferative conditions associated with the modulation of kinase activity, and particularly the inhibition of serine/threonine kinase activities. The compounds of the present invention can be used to treat proliferative disorders associated with abnormal kinase activity. As used herein, the terms "treating" and "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms.

Accordingly, one aspect of the invention is the use of a compound of the Formula (I), or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of Formula (I) or a pharmaceutically acceptable salt thereof as defined herein before.

The anti-proliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. Compounds of Formula (I) may be used sequentially with known anticancer or cytotoxic agents and treatment, including radiation when a combination formulation is inappropriate.

The term "anti-cancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyl-testosterone, prednisolone, triamcinolone, chlorotrianisene, hydroxyprogesterone, aminoglutethimide, estramustine, medroxyprogesteroneacetate, leuprolide, flutamide, toremifene, ZOLADEX®; matrix metalloproteinase inhibitors; VEGF inhibitors, such as anti-VEGF antibodies (AVASTIN®) and small molecules such as ZD6474 and SU6668; Vatalanib, BAY-43-9006, SU11248, CP-547632, and CEP-7055; HER 1 and HER 2 inhibitors including anti-HER2 antibodies (HERCEPTIN®); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; Src inhibitors, e.g., GLEEVEC® and dasatinib; CASODEX® (bicalutamide, Astra Zeneca), Tamoxifen; MEK-1 kinase inhibitors, MAPK kinase inhibitors, PI3 kinase inhibitors; PDGF inhibitors, such as imatinib; antiangiogenic and antivascular agents which, by interrupting blood flow to solid tumors, render cancer cells quiescent by depriving them of nutrition; castration, which renders androgen dependent carcinomas non-proliferative; inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, [1S-[1R*,3R*(E),7R*,10S*, 1R*,12R*,16S*]]-7-11-dihydroxy-8,8,10,12,16-pentamethyl-3-[1-methyl-2-(2-methyl-4-thiazolyl)ethenyl]-4-aza-17 oxabicyclo [14.1.0] heptadecane-5,9-dione (ixabepilone), [1S-[1R*,3R*(E), 7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione, and derivatives thereof; other CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g., 6-thioguanine and 6-mercaptopurine; glutamine antagonists, e.g., DON (AT-125; d-oxonorleucine); ribonucleotide reductase inhibitors; mTOR inhibitors; and haematopoietic growth factors.

Additional cytotoxic agents include cyclophosphamide, doxorubicin, daunorubicin, mitoxanthrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

In the field of medical oncology it is normal practice to use a combination of different forms of treatment to treat each patient with cancer. In medical oncology the other component(s) of such treatment in addition to the antiproliferative treatment defined herein may be surgery, radiotherapy or chemotherapy. Such chemotherapy may cover three main categories of therapeutic agent:

(i) antiangiogenic agents that work by different mechanisms from those defined herein before (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, borazole, exemestane), antihormones, antiprogestogens, antiandrogens (for example, flutamide, nilutamide, bicalutamide, cyproterone acetate), LHRH agonists and antagonists (for example, goseroline acetate, leuprolide), inhibitors of testosterone 5α-dihydroreductase (for example, finasteride), farnesyltransferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as AVASTIN® (bevacizumab) and ERBITUX® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); intercalating antitumour antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide, nitrosoureas, thiotepa; antimitotic agents (for example, vinca alkaloids like vincristine, vinorelbine, vinblastine and vinflunine) and taxoids such as TAXOL® (paclitaxel), Taxotere (docetaxel) and newer microbtubule agents such as epothilone analogs (ixabepilone), discodermolide analogs, and eleutherobin analogs; topoisomerase inhibitors (for example, epipodophyllotoxins such as etoposide and teniposide, amsacrine, topotecan, irinotecan); cell cycle inhibitors (for example, flavopyridols); biological response modifiers and proteasome inhibitors such as VELCADE® (bortezomib).

The present invention further provides methods of administration of compounds of Formula (I) in combination with one or more immuno-oncology agents. The immuno-oncology agents used herein, also known as cancer immunotherapies, are effective to enhance, stimulate, and/or upregulate immune responses in a subject and have a synergic effect in inhibiting tumor growth when administrated with compounds of Formula (I).

In one aspect, a compound of Formula (I) is sequentially administered prior to administration of the immuno-oncology agent. In another aspect, a compound of Formula (I) is administered concurrently with the immunology-oncology agent. In yet another aspect, a compound of Formula (I) is sequentially administered after administration of the immuno-oncology agent.

In another aspect, one or more compounds of Formula (I) may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In another aspect, the immuno-oncology agent is a cytokine that inhibits T cell activation (e.g., IL-6, IL-10, TGF-ß, VEGF, and other immunosuppressive cytokines) or a cytokine that stimulates T cell activation, for stimulating an immune response.

In one aspect, T cell responses can be stimulated by a combination of compounds of Formula (I) and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with compounds of Formula (I) for the treatment of cancer include antagonists of inhibitory receptors on NK cells or agonists of activating receptors on NK cells. For example, compounds of Formula (I) can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, compounds of Formula (I) can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In another aspect, the immuno-oncology agent is a PD-L1 antagonist, such as an antagonistic PD-L1 antibody. Suitable PD-L1 antibodies include, for example, MPDL3280A (RG7446; WO2010/077634), durvalumab (MED14736), BMS-936559 (WO2007/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO008/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO006/105021, WO009/009116) and MK-4166 (WO11/028683).

In another aspect, the immuno-oncology agent is an IDO antagonist. Suitable IDO antagonists include, for example, INCB-024360 (WO2006/122150, WO07/75598, WO08/36653, WO08/36642), indoximod, or NLG-919 (WO09/73620, WO009/1156652, WO11/56652, WO12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO006/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO 11/109400).

As stated above, the Formula (I) compounds of the invention are of interest for their antiproliferative effects. Such compounds of the invention are expected to be useful in a wide range of disease states including cancer, psoriasis, and rheumatoid arthritis.

More specifically, the compounds of Formula (I) are useful in the treatment of a variety of cancers, including (but not limited to) the following:
  carcinoma, including that of the prostate, pancreatic ductal adenocarcinoma, breast, colon, lung, ovary, pancreas, and thyroid;
  tumors of the central and peripheral nervous system, including neuroblastoma, glioblastoma, and medulloblastoma; and
  other tumors, including melanoma and multiple myeloma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neurofibromatosis, pulmonary fibrosis, arthritis, psoriasis, glomerulonephritis, restenosis following angioplasty or vascular surgery, hypertrophic scar formation and inflammatory bowel disease.

The compounds of Formula (I) are especially useful in treatment of tumors having a high incidence of serine/threonine kinase activity, such as prostate, colon, brain, thyroid and pancreatic tumors. Additionally, the compounds of the invention may be useful in treatment of sarcomas and pediatric sarcomas. By the administration of a composition (or a combination) of the compounds of this invention, development of tumors in a mammalian host is reduced.

Compounds of Formula (I) may also be useful in the treatment of other cancerous diseases (such as acute myelogenous leukemia) that may be associated with signal transduction pathways operating through kinases such as DYRK1a, CDK, and GSK3β. The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th ed. (1985), which is incorporated herein by reference in its entirety.

The pharmaceutical compositions of the invention containing the active ingredient may be in a form suitable for oral use, for example, as Tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The pharmaceutical compositions may be in the form of sterile injectable aqueous solutions. Among the acceptable vehicles and solvents that may be employed are water, Ringer's solution and isotonic sodium chloride solution. The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS® Model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of Tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as Plastibase (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release Tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried Tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., Gantrez); and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

When a compound according to this invention is administered into a human subject, the daily dosage will normally be determined by the prescribing physician with the dosage generally varying according to the age, weight, sex and response of the individual patient, as well as the severity of the patient's symptoms. Exemplary dosage amounts for a mammal may include from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, which are affected by mediation of protein kinase enzyme levels.

If formulated as a fixed dose, a combination product can, for example, utilize a dosage of the compound of Formula (I)-(III) within the dosage range described above and the dosage of another anti-cancer agent/treatment within the approved dosage range for such known anti-cancer agent/treatment. If a combination product is inappropriate, the compounds of Formula (I)-(III) and the other anti-cancer agent/treatment can, for example, are administered simultaneously or sequentially. If administered sequentially, the present invention is not limited to any particular sequence of administration. For example, compounds of Formulas (I)-(III) can be administered either prior to, or after, administration of the known anti-cancer agent or treatment.

BIOLOGICAL ASSAYS

A. CK2 Kinase Assay:

The effectiveness of compounds of the present invention as inhibitors of protein kinases can be readily tested by assays known to those skilled in the art. For example, in vitro protein kinase assays may be conducted with a relevant purified protein kinase and an appropriate synthetic substrate to determine the inhibitory activity of the compounds. Assays for inhibition of CK2 by the instant compounds were performed in 384-well plates with reaction mixtures containing 10 µM of peptide substrate (RRRADDSDDDDD-NH2), [γ-$^{33}$P]ATP (10 µCi) at 25 µM (CK2A1) or 5 µM (CK2A2), 20 mM Hepes (pH 7.4), 100 mM NaCl, 10 mM MgCl$_2$, 0.25 mM dithiothreitol, Brij-35 at 0.015%, and recombinant CK2A1 (10 nM, Invitrogen) or CK2A2 (5 nM, Upstate Biotechnology). Reaction mixtures were incubated at 30° C. for 1 hour, and reaction products were captured by binding to phosphocellulose (P81) filter plates. Incorporation of radioactive phosphate into the peptide substrate was determined by liquid scintillation counting. The potency of compounds in inhibiting CK2 is expressed as IC$_{50}$, defined as the concentrations of compounds required to inhibit the enzymatic activity by 50%.

The inhibitory activity of the instant compounds may also be measured by recombinant CK2 holoenzyme kinase assays. The assays were performed in U-bottom 384-well plates. The final assay volume was 30 µl prepared from 15

μl additions of enzyme and substrates (fluoresceinated peptide FL-RRRADDSDDDDD-NH2 and ATP) and test compounds in assay buffer (20 mM HEPES pH 7.4, 10 mM MgCl$_2$, 100 mM NaCl, 0.015% Brij35 and 0.25 mM DTT). The reaction was initiated by the combination of bacterially expressed, CK2 α/β or CK2 α'/β holoenzyme with substrates and test compounds. The reaction was incubated at room temperature for 60 minutes and terminated by adding 30 μl of 35 mM EDTA to each sample. The reaction mixture was analyzed on the Caliper LABCHIP® 3000 (Caliper, Hopkinton, Mass.) by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the CK2 α/β assay was 25 μM ATP, 1.5 μM FL-RRRADDSDDDDD-NH2, 50 pM CK2 α/β holoenzyme, and 1.6% DMSO. The final concentration of reagents in the CK2 α'/β assay was 10 μM ATP, 1.5 μM FL-RRRADDSDDDDD-NH2, 100 pM CK2 α'/β holoenzyme, and 1.6% DMSO. Dose response curves were generated to determine the concentration required inhibiting 50% of kinase activity (IC$_{50}$). Compounds were dissolved at 10 mM in dimethylsulfoxide (DMSO) and evaluated at eleven concentrations. IC$_{50}$ values were derived by non-linear regression analysis.

The IC$_{50}$ value ranges of the compounds of the present invention obtained in the CK2 kinase assays described above are shown in Table A.

TABLE A

| Example No. | CK2A1 (IC$_{50}$, nM) | CK2A2 (IC$_{50}$, nM) |
|---|---|---|
| 1 | +++ | +++ |
| 2 | + | ++ |
| 3 | + | ++ |
| 4 | ++ | +++ |
| 5 | + | ++ |

+++: IC$_{50}$ <10 nM;
++: IC$_{50}$ - between 10 and 100 nM;
+: IC$_{50}$ - between 100 and 1000 nM B. Cell Proliferation Inhibition Assay:

Compounds were evaluated for their ability to inhibit cell proliferation, using an assay that measures mitochondrial metabolic activity that is directly correlated with cell numbers. Cells were plated at 2000 cells/well in 96-well plates and were cultured for 24 h in RPMI-1640 supplemented with 2% fetal bovine serum, before test compounds were added. Compounds were diluted in culture medium such that the final concentration of dimethyl sulfoxide never exceeded 1%. Following the addition of compounds, the cells were cultured for an additional 72 h before cell viability was determined by measuring the conversion of 3-(4,5-dimethylthiazol-2-yl)-2,5-diphenyltetrazolium bromide (MTT) dye using the CellTiter96 kit (Promega) or by measuring the conversion of [3-(4,5-dimethylthiazol-2-yl)-5-(3-carboxymethoxyphenyl)-2-(4-sulfophenyl)-2H-tetrazolium (MTS) dye using the CELLTITER 96® AQueous (Promega).

In addition to the anti-CK2 activity, The compounds of Formula (I) of the present invention when R$_2$ is H possess surprisingly enhanced pharmacokinetic (PK) and pharmacodynamic (PD) properties over the compounds disclosed in WO 2014/011974. In the in vivo comparative PK and PD studies shown below, Example 1 of the present invention demonstrate superior efficacy and bioavailability over Example 174 of WO 2014/011974 at pages 175-176.

Example 1

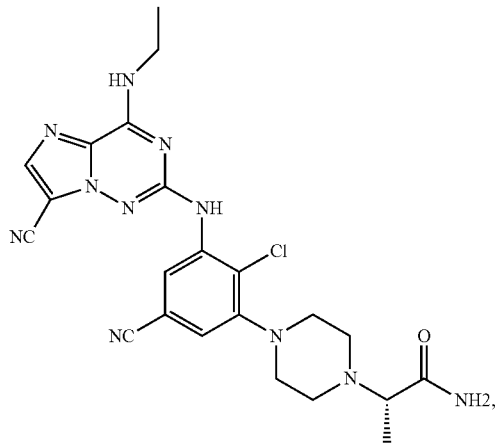

Example 174

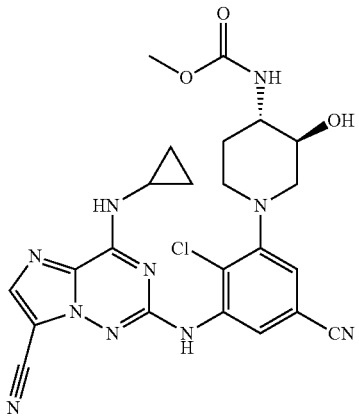

C. In Vivo Pharmacodynamic Study:

pCK2 motif is a putative cellular substrate of CK2 with molecular weight of ~60 kDa. The intensity of this band has been shown to be modulated by several chemical and biological (e.g. siRNA) inhibitors of CK2. Prolonged and strong inhibition of pCK2 motif is necessary to demonstrate robust in vivo efficacy in antitumor models.

To determine extent of pCK2 motif inhibition by test compounds in vivo, SNU-C1 colon tumor cells were inoculated into female BALB/c athymic mice and propagated as subcutaneous xenografts. The dosing solutions of the compound or control were administered to mice with tumors reaching ~500 mm by oral gavage at the indicated dose levels and schedules. Tumors were collected from control and treated mice at the indicated times and immediately frozen in liquid nitrogen. Frozen tumors were thawed on ice in 5 volumes of TTG buffer (Tris-HCl, pH 7.9, 10% glycerol, 0.02% Tween-20). Tumors were homogenized using a Qiagen TissueLyser II (3×1 min (1/30S)) in Qiagen Tissulyser tubes containing steel beads. Tumor homogenates were clarified by microcentrifugation at 13000 rpm for 10 min. Western blot analysis was performed using 60 μg of protein per lane on 4-15% BioRad SDS-PAGE gels. Blots were probed with an anti-pCK2 motif antibody (mAb #8738 Cell Signaling Technology) and anti-Actin antibody. The pCK2 motif antibody is a purified polyclonal antibody developed by immunizing mice with a degenerate mixture of peptides corresponding to the consesnus phorylation site used by CK2. The intensity of the pCK2 motif band was measured on images obtained from the Licor Odyssey instrument. % pCK2 remaining at each dose was calculated relative to the average intensity of bands from untreated, control mouse tumors.

As shown in Table B, Example 1 of the present invention significantly suppressed the pCK2 motif levels relative to vehicle control up to 24 hours at a dose of 15 mg/kg BID. In contrast, the suppressive effect of Example 174 of WO 2014/011974 was much less robust than Example 1 at the highest possible exposure in mice.

TABLE B

In vivo pharamacodynamic response of Examples 1 and 174 in SNU-C1 (colon) xenograft tumor model in mice

| Example | % inh. of p-CK2/Dose at 24th hour |
| --- | --- |
| 174 (WO2014011974) | 33%/40 mg/kg BID |
| 1 | 91%/15 mg/kg BID |

C. Single-Dose Pharmacokinetics in Rats:

In a study to determine oral bioavailability in male Sprague-Dawley rats, two groups of animals (N=3 per group, 300 to 350 g) are used. One group (non-fasted) receives the compound by IV infusion (over 10 minutes) via a jugular vein and one group (fasted) receives drug by oral gavage. Serial blood samples (~0.3 mL) are collected from the jugular vein into tri-potassium ethylenediaminetetraacetic acid (K3EDTA)-containing tubes at 0.167 (for IV), 0.25, 0.5, 1, 3, 5, 7, and 24 hours, post dose and then centrifuged at 4° C. (1500 to 2000×g) to obtain plasma, which is stored at −20° C. until analysis by LC-MS/MS.

The pharmacokinetic parameters were obtained by non-compartmental analysis of plasma concentration (determined by LC/MS/MS) vs. time data (ThermoKinetica Software version 4.4.1). The peak concentration (Cmax) and time for Cmax, Tmax, were recorded directly from experimental observations. The area under the curve from time zero to the last sampling time (AUC0-t) was calculated using a combination of linear and log trapezoidal summations. The total plasma clearance (CLTp), steady-state volume of distribution (Vss), apparent elimination half-life (t½) and mean residence time (MRT) were estimated after IV administration. Estimation of T½ was made using a minimum of 3 time points with quantifiable concentrations.

For non-prodrugs, the absolute oral bioavailability F was estimated as the ratio of dose-normalized AUC values following oral and IV doses. As shown in Table C, Example 1 of the present invention showed marked improvement in bioavailability in rats as compared to Example 174 of WO2014011974.

TABLE C

Oral Bioavailability in Rats

| Example | % F |
| --- | --- |
| 174 (WO2014011974) | 8 |
| 1 | 68 |

In case of prodrugs (e.g., Examples 2 and 5), absolute bioavailability F was estimated as the ratio of dose-normalized AUC values of parent (Example 1) upon oral administration of prodrugs (Examples 2 and 5) and IV infusion of parent (Example 1).

TABLE D

Prodrug bioavailability in Rats

| Example | % F |
| --- | --- |
| 2 | 40 |
| 5 | 88 |

D. Thermodynamic Equilibrium Aqueous Solubility Assay:

Standards Preparation: The calibration standard was prepared by accurately weighing 0.5-0.7 mg of sample in 5 ml of methanol. If the material was not fully soluble in methanol, other solvents such as DMSO or mixed solvents were used.

Test Sample Preparation: An excess amount of sample was equilibrated with 1 mL of buffer (50 mM potassium phosphate, pH 6.5 and 50 mM sodium acetate, pH 4.0) in a 2 mL glass vial. The solution was sonicated and vortexed for ~30 seconds. The vials were shaken at 300 rpm at room temperature for 24 hrs. The exact incubation time for a specific prodrug was based on the prior aqueous stability data. If the compound was stable in the buffer up to 24 hrs, then the solubility was measured after 24 hrs, otherwise kinetic solubility data was reported. The final saturated solution was then transferred to a 1.5 mL eppendorf tube and centrifuged for ~2 min. at 10000 rpms. The supernatant from the saturated solution was transferred to a glass HPLC vial and the solubility was analyzed by HPLC using a four point calibration curve.

As shown in Table E, the prodrug compounds (Examples 2 and 5) of the present invention demonstrate superior solubility over the parent compound (Example 1).

TABLE E

Solubility Data

| | Solubility (µg/mL) | | |
| --- | --- | --- | --- |
| Example | pH 1.0 | pH 4.0 | pH 6.5 |
| 1 | 22 | ND* | <1 |
| 2 | 242 | 124 | 835 |
| 5 | 253 | 160 | 1343 |

*not determined

Methods of Preparation

The compounds of the present invention may be prepared by methods such as those illustrated in the following schemes. Solvents, temperatures, pressures, and other reaction conditions may readily be selected by one of ordinary skill in the art. Starting materials are commercially available or readily prepared by one of ordinary skill in the art. These schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). All documents cited herein are incorporated herein by reference in their entirety.

In general, the time taken to complete a reaction procedure will be judged by the person performing the procedure, preferably with the aid of information obtained by monitoring the reaction by methods such as HPLC or TLC. A reaction does not have to go to completion to be useful to this invention. The methods for the preparation of various heterocycles used to this invention can be found in standard organic reference books, for example, Katritzky, A. R. et al., eds., *Comprehensive Heterocyclic Chemistry, The Structure, Reactions, Synthesis and Uses, of Heterocyclic Compounds*, First Edition, Pergamon Press, New York (1984), and Katritzky, A. R. et al., eds., *Comprehensive Heterocyclic Chemistry II, A Review of the Literature 1982-1995: The Structure, Reactions, Synthesis and Uses, of Heterocyclic Compounds*, Pergamon Press, New York (1996).

Unless otherwise specified, the various substituents of the compounds are defined in the same manner as the Formula (I) compound of the invention.

Compounds of general formula (I) may be prepared by as described in Scheme A. Displacement of halide in Boc-protected aniline 1 with nitrogen containing monocyclic saturated heterocycle 2 using Pd(0) mediated reaction followed by Boc-deprotection would give aniline 3. Coupling of aniline 3 with suitably protected imidazo[2,1-f][1,2,4]triazine chloride 4 (prepared using procedure in WO2014011974) using Pd(0) catalyzed reaction would afford intermediate 5. Coupling of intermediate 5 with chloromethyl chloroformate would give chloromethyl carbamate intermediate 6. Coupling of 6 with $R_5CO_2H$ followed by global deprotection would afford I.

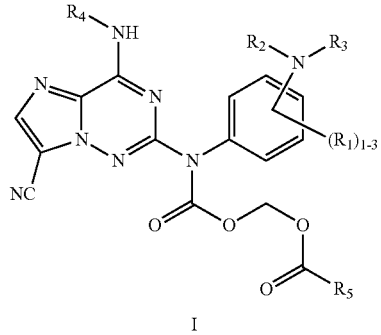

In case of heterocycle 2 containing additional functional groups (e.g. hydroxyl, amino) suitable orthogonal protective group could be employed in the reaction sequence.

Alternatively, Compounds of general formula (I) may be prepared by as described in Scheme B. Coupling of aniline 3 with suitably protected imidazo[2,1-f][1,2,4]triazine chloride 7 (prepared using procedure in WO2014011974) using Pd(0) catalyzed reaction would afford intermediate 8. Removal of p-methoxybenyl protective group followed by reprotection of both aniline nitrogen with Boc would afford intermediate 9. Displacement of $R_4$—N-Boc with amine ($R_4NH_2$), followed by CBz protection and Boc removal would give intermediate 10. Coupling of intermediate 10 with chloromethyl chloroformate would give chloromethyl carbamate intermediate 11. Coupling of 11 with $R_5CO_2H$ followed by global deprotection would afford I.

Scheme A

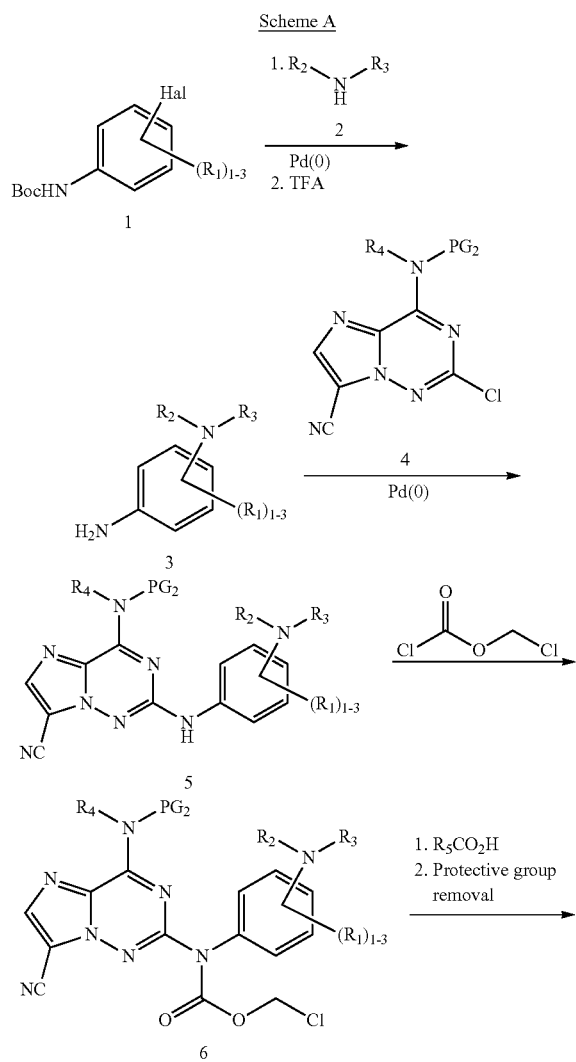

Scheme B

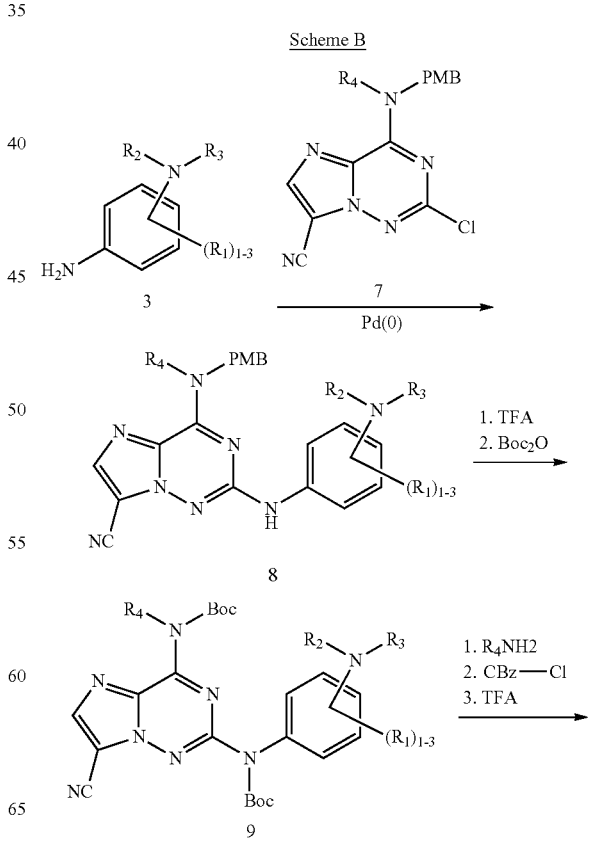

-continued

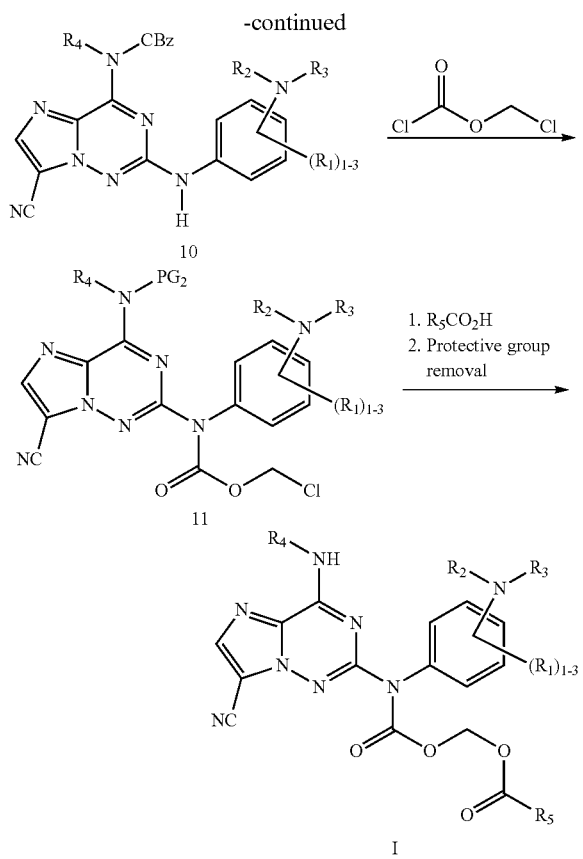

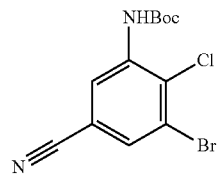

EXAMPLES

The following Examples illustrate embodiments of the inventive compounds and starting materials, and are not intended to limit the scope of the claims. For ease of reference, the following abbreviations are used herein:
Aq=aqueous
BOC=tert-butoxycarbonyl
bp=boiling point
Bu=butyl
DMAP=4-dimethylaminopyridine
DIPEA or DIEA=N,N-diisopropylethylamine
DME=1,2-dimethoxyethane
DMF=dimethyl formamide
EDCI=1-3-dimethylaminopropyl)-3-ethylcarbodiimide
Et=ethyl
Et$_2$O=diethyl ether
HOBT=1-hydroxybenzotriazole
EtOAc=ethyl acetate
EtOH=ethanol
g=gram(s)
H=hydrogen
l=liter
mCPBA—meta chloro perbenzoic acid
Me=methyl
MeCN=acetonitrile
MeOH=methanol
NMP=1-methyl-2-pyrrolidinone
Ph=phenyl
Pr=propyl
PS=polystyrene
TEA=triethylamine
TFA=trifluoroacetic acid
mg=milligram(s)
ml or mL=milliliter
μl=microliter
mmol=millimole
μmol=micromole
mol=mole
mp=melting point
room temperature=room temperature
HPLC=high pressure liquid chromatography
LC/MS=liquid chromatography/mass spectrometry Preparation of Intermediates Intermediate 1 tert-butyl 3-bromo-2-chloro-5-cyanophenylcarbamate

Step 1—Preparation of 3,5-dibromo-4-hydroxybenzonitrile (I1A)

To a solution of 4-hydroxybenzonitrile (1 g, 8.39 mmol) in acetic acid (20 mL) was added bromine (1.038 mL, 20.15 mmol) dropwise at room temperature. The mixture was stirred for 30 minutes. The mixture was poured onto ice; the solid was collected by filtration, rinsed with water and dried to give 3,5-dibromo-4-hydroxybenzonitrile as white solid product (2.25 g, 65% yield).
MS (ESI): m/z 277 (M+H)
1H NMR (400 MHz, CHLOROFORM-d) δ ppm 7.77 (2H, s), 6.37 (1H, br. s.)

Step 2—Preparation of 3,5-dibromo-4-hydroxybenzonitrile (I1B)

To a suspension of 3,5-dibromo-4-hydroxybenzonitrile (2.11 g, 7.62 mmol) in acetic acid (70 mL) was added sodium nitrite (2.63 g, 38.1 mmol) in small portion, evolving bubbles and bromine were observed. After addition, the mixture was stirred at 50° C. overnight. The reaction was cooled to room temperature; water (250 ml) was added and extracted with EtOAc for two times. The combined extracts were washed with water and brine, dried over MgSO$_4$ filtered and the filtrate was concentrated to give yellow orange solid. The solid was treated with a small amount of MeOH, collected by filtration, rinsed with MeOH, dried to afford 3-Bromo-4-hydroxy-5-nitrobenzonitrile as a yellow solid (1.56 g, 69% yield)
1H NMR (400 MHz, CHLOROFORM-d) δ ppm 7.26 (2H, s), 8.11 (1H, d, J=1.72 Hz), 8.44 (1H, d, J=1.94 Hz)

Step 3—Preparation of 3-bromo-4-chloro-5-nitrobenzonitrile (I1C)

DMF (2 mL) was cooled to −20° C. and treated gradually in a dropwise manner with oxalyl chloride (0.216 ml, 2.469 mmol). After 10 min, a solution of 3-bromo-4-hydroxy-5-nitrobenzonitrile (200 mg, 0.823 mmol) in DMF (2 mL) was added slowly via syringe while maintaining an internal temperature below −10° C. After addition, the mixture was allowed to warm to room temperature and then heated at 100° C. for 1.5 h. The reaction mixture was cooled and poured into ice-water; the solid was collected by filtration, rinsed with water and dried to give 3-bromo-4-chloro-5-nitrobenzonitrile as tan solid (172 mg, 72% yield).

1H NMR (400 MHz, CHLOROFORM-d) δ ppm 8.13 (1H, d, J=1.76 Hz), 8.02 (1H, d, J=1.98 Hz)

Step 4—Preparation of 3-amino-5-bromo-4-chlorobenzonitrile (I1D)

A mixture of 3-bromo-4-chloro-5-nitrobenzonitrile (0.99 g, 3.79 mmol), iron (1.057 g, 18.93 mmol) and ammonium chloride (2.025 g, 37.9 mmol) in THF, MeOH and water (60 ml, 1:1:1) was heated to reflux for 1 h. More iron (0.5 g) and $NH_4Cl$ (2 g) added, heated for another 2 h and then cooled to room temperature. Filtered off solid, the filtrate was concentrated to remove the organic solvent. The residue was diluted with water, extracted with EtOAc twice, dried and concentrated to dryness. The resulting solid was triturated with EtOAc, solid was filtered off through celite pad and the filtrate was concentrated to afford 3-amino-5-bromo-4-chlorobenzonitrile as yellow solid which was used as such in the next reaction (0.88 g, 65% yield).

Step 5—Preparation of Intermediate 1

To a solution of 3-amino-5-bromo-4-chlorobenzonitrile (0.88 g, 3.80 mmol) in DCM (25 mL) was added TEA (1.590 mL, 11.41 mmol), $BOC_2O$ (1.059 mL, 4.56 mmol) and DMAP (0.464 g, 3.80 mmol). The mixture was stirred at room temperature for 16 h. The reaction mixture was concentrated, the crude product was purified using ISCO silica gel column (24 g, EtOAc/hexane=0-30%) to give tert-butyl 3-bromo-2-chloro-5-cyanophenylcarbamate as white solid (0.667 g, 80% yield)

MS (ESI): m/z 331 (M+H)

1H NMR (400 MHz, CHLOROFORM-d) δ ppm 8.62 (1H, d, J=1.76 Hz), 7.59 (1H, d, J=1.98 Hz), 7.21 (1H, br. s.), 1.57 (9H, s)

WO2014011974) (10 g, 37.3 mmol) in anhydrous THF (300 ml) was treated with N-(4-methoxybenzyl)ethanamine (8.0 ml, 46.7 mmol), resulting in the immediate precipitation of a solid. The reaction was stirred for 1 hour; the mixture was concentrated in vacuo. To the residue was added EtOAc (100 ml) and the mixture stirred 10 min. The salts were filtered off and the filtrate was washed with 0.5M citric acid, sat. $NaHCO_3$, water and brine. The solution was dried over $Na_2SO_4$ and solvents removed to afford 7-bromo-2-chloro-N-ethyl-N-(4-methoxybenzyl)imidazo[2,1-f][1,2,4]triazin-4-amine (15.8 g, 62% yield).

MS (ESI): m/z 398 (M+H)

$^1$H NMR (500 MHz, DMSO-$d_6$) δ 7.80 (d, J=17.5 Hz, 1H), 7.37-7.31 (m, 1H), 7.28 (d, J=8.7 Hz, 1H), 6.90 (dd, J=12.3, 8.8 Hz, 2H), 5.67 (s, 1H), 4.93 (s, 1H), 4.39-4.22 (m, 1H), 3.74 (d, J=4.3 Hz, 3H), 3.67-3.54 (m, 1H), 1.27-1.09 (m, 3H)

Step 2: Preparation of Intermediate 2

To an oven dried 500 ml round bottom flask was added 7-bromo-2-chloro-N-ethyl-N-(4-methoxybenzyl)imidazo[2,1-f][1,2,4]triazin-4-amine (12.5 g, 31.5 mmol) and copper(I) cyanide (9.0 g, 100 mmol). The flask was caped under nitrogen and NMP (250 mL) was added. The mixture stirred 5 min at 25° C. and the flask was evacuated and back-filled with nitrogen. The reaction stirred at 135° C. (oil bath) 21 hr. The reaction cooled to 25° C., diluted with ethyl acetate (500 ml) and filter through celite bed. The bed was washed with EtOAc 3×100 ml and the filtrate washed with water 1×300 ml and brine 3×150 ml. The organics dried with sodium sulphate and remove solvent. The material was crystallized from IPA and filtered to afford 2-chloro-4-(ethyl(4-methoxybenzyl)amino)imidazo[2,1-f][1,2,4]triazine-7-carbonitrile (11 g, 62% yield).

MS (ESI): m/z 343 (M+H)

$^1$H NMR (500 MHz, DMSO-$d_6$) δ 8.41 (d, J=16.2 Hz, 1H), 7.42-7.27 (m, 2H), 6.97-6.85 (m, 2H), 5.66 (s, 1H), 4.95 (s, 1H), 4.33-4.23 (m, 1H), 3.74 (d, J=3.5 Hz, 3H), 3.62 (d, J=7.0 Hz, 1H), 1.30-1.10 (m, 3H)

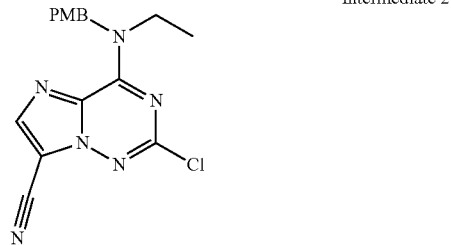

Intermediate 2

2-chloro-4-(ethyl(4-methoxybenzyl)amino)imidazo[2,1-f][1,2,4]triazine-7-carbonitrile Step 1—Preparation of 7-bromo-2-chloro-N-ethyl-N-(4-methoxybenzyl)imidazo[2,1-f][1,2,4]triazin-4-amine (I2A)

A solution of 7-bromo-2,4-dichloroimidazo[2,1-f][1,2,4]triazine (prepared according to procedure in

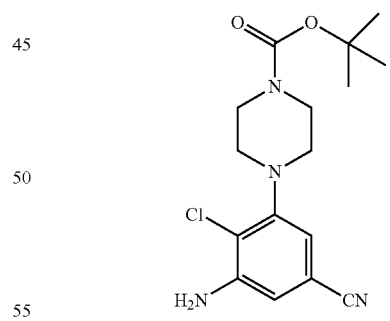

Intermediate 3 tert-butyl 4-(3-amino-2-chloro-5-cyanophenyl)piperazine-1-carboxylate

Step 1—Preparation of tert-butyl 4-(3-((tert-butoxycarbonyl) amino)-2-chloro-5-cyanophenyl) piperazine-1-carboxylate (I3A)

Tert-butyl (3-bromo-2-chloro-5-cyanophenyl) carbamate (Intermediate 1) (4.5 g, 13.57 mmol), $Pd_2dba_3$ (0.746 g, 0.814 mmol), BINAP (0.676 g, 1.086 mmol) and $Cs_2CO_3$ (8.84 g, 27.1 mmol) were suspended in toluene (12.0 mL) at room temperature. Tert-butyl piperazine-1-carboxylate (3.29 g, 17.64 mmol) was added and the reaction was degassed and purged with Argon. The reaction mixture was heated at 105° C. for overnight. On completion of the reaction, the reaction mixture was cooled to room temperature, diluted with ethyl acetate, filtered through celite and concentrated. The crude material was purified by ISCO silica gel column chromatography, using 0-10% ethyl acetate-hexane as eluent. Pure fractions were concentrated to obtain tert-butyl 4-(3-((tert-butoxycarbonyl) amino)-2-chloro-5-cyanophenyl) piperazine-1-carboxylate (3.0 g, 65% yield) as an off-white solid.

MS (ESI): m/z 437.2 (M+H)

Step 2—Preparation of 3-amino-4-chloro-5-(piperazin-1-yl)benzonitrile (I3B)

To the stirred solution of tert-butyl 4-(3-((tert-butoxycarbonyl)amino)-2-chloro-5-cyanophenyl)piperazine-1-carboxylate (2.0 g, 4.58 mmol) in dichloromethane (40 mL) was added trifluoroacetic acid (8.89 mL, 115 mmol) slowly drop wise at room temperature and the reaction mixture was stirred for 3 hours. On completion of the reaction, the reaction mixture was diluted with methylene chloride (300 mL), cooled to 0° C., basified with ammonia solution and extracted twice. The organic layer was washed with brine, dried over anhydrous sodium sulfate and concentrated. The crude material was washed with diethyl ether several times and dried under vacuum to give 3-amino-4-chloro-5-(piperazin-1-yl)benzonitrile (1.0 g, 90% yield) as a brown color solid.

MS (ESI): m/z 237.5 (M+H)

Step 3—Preparation of Intermediate 3

To the stirred solution of 3-amino-4-chloro-5-(piperazin-1-yl)benzonitrile (1.0 g, 4.22 mmol) in dichloromethane (10 mL) was added Boc$_2$O (0.981 mL, 4.22 mmol) at 0° C., dropwise over a period of 10 minutes followed by triethylamine (0.883 mL, 6.34 mmol). The reaction mixture was allowed to warm to room temperature and stirred for 1 hour. The reaction mixture was diluted with methylene chloride (100 mL), washed with brine (30 mL), dried over Na$_2$SO$_4$ and concentrated at to get crude product as brown solid which was washed with diethyl ether four times and dried under vacuum to afford tert-butyl 4-(3-amino-2-chloro-5-cyanophenyl)piperazine-1-carboxylate (1.4 g, 89% yield) as an off-white solid.

MS (ESI): m/z 335.1 (M+H)

Example 1

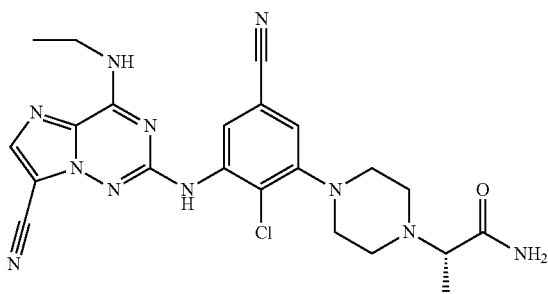

(S)-2-(4-(2-chloro-5-cyano-3-((7-cyano-4-(ethylamino)imidazo[2,1-f][1,2,4]triazin-2-yl)amino)phenyl)piperazin-1-yl)propanamide Step 1—Preparation of tert-butyl 4-(2-chloro-5-cyano-3-((7-cyano-4-(ethyl(4-methoxybenzyl)amino)imidazo [2,1-f][1,2,4]triazin-2-yl)amino)phenyl)piperazine-1-carboxylate (1A)

Nitrogen gas was bubbled into a stirred solution of 2-chloro-4-(ethyl(4-methoxybenzyl)amino)imidazo[2,1-f][1,2,4]triazine-7-carbonitrile (intermediate 2) (6.11 g, 17.81 mmol), tert-butyl 4-(3-amino-2-chloro-5-cyanophenyl)piperazine-1-carboxylate (intermediate 3)(6 g, 17.81 mmol), palladium(II) acetate (0.400 g, 1.781 mmol), DPPF (0.988 g, 1.781 mmol), XANTPHOS (1.031 g, 1.781 mmol) and Cs$_2$CO$_3$ (11.61 g, 35.6 mmol) for 2 minutes and then stirred at 75° C. under nitrogen atmosphere for 1 hr. The reaction was diluted with ethyl acetate, the catalyst was removed by filtration through a pad of celite and the filtrate was concentrated. The crude material was purified by flash chromatography on silica gel using ISCO silica gel column chromatography, using dichloromethane-ethyl acetate (0-10%) to yield tert-butyl 4-(2-chloro-5-cyano-3-((7-cyano-4-(ethyl (4-methoxybenzyl)amino)imidazo [2,1-f][1,2,4]triazin-2-yl) amino)phenyl)piperazine-1-carboxylate (10.58 g, 92% yield).

MS (ESI): m/z 643.4 (M+H)

Step 2—Preparation of 2-((2-chloro-5-cyano-3-(piperazin-1-yl)phenyl)amino)-4-(ethyl(4-methoxybenzyl)amino)imidazo [2,1-f][1,2,4]triazine-7-carbonitrile (1B)

TMS-OTf (8.92 mL, 49.4 mmol) was added dropwise to a cooled (0° C.) solution of tert-butyl 4-(2-chloro-5-cyano-3-((7-cyano-4-(ethyl(4-methoxybenzyl)amino)imidazo[2,1-f][1,2,4]triazin-2-yl)amino)phenyl)piperazine-1-carboxylate (10.58 g, 16.45 mmol) and 2,6-lutidine (5.75 mL, 49.4 mmol) in dichloromethane (200 mL). The reaction mixture was stirred for 3 hours at the same temperature. The reaction mixture was neutralized with ammonium hydroxide solution, and extracted with dichloromethane (3×100 mL), washed with brine solution, dried over sodium sulphate, filtered and concentrated in vaccuo. The crude material was purified by flash chromatography on silica gel using ISCO silica gel chromatography, eluting with dichloromethane-20% (2M NH$_3$/MeOH) in dichloromethane to give 2-((2-chloro-5-cyano-3-(piperazin-1-yl)phenyl)amino)-4-(ethyl (4-methoxybenzyl)amino)imidazo [2,1-f][1,2,4]triazine-7-carbonitrile (7.83 g, 88% yield).

MS (ESI): m/z 543.3 (M+H)
1H NMR (400 MHz, CHLOROFORM-d) δ 8.48 (d, J=1.8 Hz, 1H), 7.93 (d, J=10.1 Hz, 1H), 7.48-7.35 (m, 1H), 7.27-7.21 (m, 2H), 7.07-6.97 (m, 1H), 6.94-6.83 (m, 2H), 5.70 (s, 1H), 5.00 (s, 1H), 4.39 (d, J=7.0 Hz, 1H), 3.82 (s, 3H), 3.77 (d, J=7.0 Hz, 1H), 3.10 (d, J=4.6 Hz, 4H), 3.03 (br. s., 3H), 1.43-1.24 (m, 3H)

Step 3—Preparation of (R)-1-amino-1-oxopropan-2-yl Methanesulfonate (1C)

Methanesulfonyl chloride (1.924 mL, 24.69 mmol) was added to a −40° C. stirred solution of (R)-(+)-lactamide (2 g, 22.45 mmol) and triethylamine (3.44 mL, 24.69 mmol) in THF (100 mL). The reaction mixture was brought to room temperature and stirred for 1 h. The reaction mixture was filtered to remove triethylamine salt and the filtrate was concentrated. The crude material was purified by flash chromatography on silica gel using ISCO system, eluting with 0% to 40% in 10 mins (dichloromethane in 20% (2M NH₃/MeOH)/80% dichloromethane) to afford (R)-1-amino-1-oxopropan-2-yl methanesulfonate (2.13 g, 12.74 mmol, 56.8% yield)

MS (ESI): m/z 168.0 (M+H)

1H NMR (400 MHz, DMSO-d6) δ 7.55 (br. s., 1H), 7.41 (br. s., 1H), 4.92 (q, J=6.7 Hz, 1H), 3.24 (s, 3H), 1.45 (d, J=6.8 Hz, 3H)

Step 4—Preparation of (S)-2-(4-(2-chloro-5-cyano-3-((7-cyano-4-(ethyl(4-methoxybenzyl)amino)imidazo [2,1-f][1,2,4]triazin-2-yl)amino)phenyl)piperazin-1-yl)propanamide (1D)

A stirred solution of 2-((2-chloro-5-cyano-3-(piperazin-1-yl)phenyl)amino)-4-(ethyl(4-methoxybenzyl)amino)imidazo[2,1-f][1,2,4]triazine-7-carbonitrile (3 g, 5.52 mmol) in acetonitrile (50 mL) was treated with DIPEA (2.89 mL, 16.57 mmol) and followed by (R)-1-amino-1-oxopropan-2-yl methanesulfonate (1.385 g, 8.29 mmol), the reaction mixture was stirred at 70° C. for 2 days. The reaction was quenched with half saturated NH₄Cl solution, extracted with ethyl acetate (3×75 mL), combined organic extracts were dried over Na₂SO₄, filtered and concentrated. The crude material was purified by ISCO silica gel chromatography, eluting with 0% to 15% in 10 mins (dichloromethane in 20% (2M NH₃/MeOH)/80% dichloromethane) to yield (S)-2-(4-(2-chloro-5-cyano-3-((7-cyano-4-(ethyl(4-methoxybenzyl) amino)imidazo [2,1-f][1,2,4]triazin-2-yl)amino)phenyl)piperazin-1-yl)propanamide (3 g, 88% yield)

MS (ESI): m/z 614.2 (M+H)

Step 5—Preparation of (S)-2-(4-(2-chloro-5-cyano-3-((7-cyano-4-(ethylamino)imidazo[2,1-f][1,2,4]triazin-2-yl)amino)phenyl)piperazin-1-yl)propanamide (1E)

A stirred solution of (S)-2-(4-(2-chloro-5-cyano-3-((7-cyano-4-(ethyl(4-methoxybenzyl)amino)imidazo[2,1-f][1,2,4]triazin-2-yl)amino)phenyl)piperazin-1-yl)propanamide (1 g, 1.628 mmol) in dichloromethane (15 mL) was treated with anisole (0.178 mL, 1.628 mmol), followed by TFA (3.14 mL, 40.7 mmol) and the resulting mixture was stirred at ambient temperature for 5 hrs The reaction was concentrated and the residue was triturated with ether. The resulting solid was collected by filtration, rinsed with ether and air dried. The solid was suspended in methanol (10 mL), neutralized with 7.0 N ammonia in methanol, and stirred at ambient temperature for 1 hr. The white solid was collected by filtration and rinsed with methanol and dried in vacuo to afford (S)-2-(4-(2-chloro-5-cyano-3-((7-cyano-4-(ethylamino)imidazo[2,1-f][1,2,4]triazin-2-yl)amino)phenyl)piperazin-1-yl)propanamide (0.66 g, 79% yield)

MS (ESI): m/z 494.5 (M+H)

1H NMR (400 MHz, DMSO-d6) δ 9.18 (t, J=5.7 Hz, 1H), 8.85 (s, 1H), 8.19 (s, 1H), 7.96 (d, J=1.7 Hz, 1H), 7.32 (d, J=1.7 Hz, 1H), 7.24 (br. s., 1H), 7.03 (br. s., 1H), 3.53-3.41 (m, 2H), 3.06 (d, J=6.5 Hz, 5H), 2.74-2.58 (m, 4H), 1.19 (t, J=7.2 Hz, 3H), 1.13 (d, J=7.0 Hz, 3H)

Step 6—Preparation of Example 1

A stirred suspension of (S)-2-(4-(2-chloro-5-cyano-3-((7-cyano-4-(ethylamino)imidazo[2,1-f][1,2,4]triazin-2-yl) amino)phenyl)piperazin-1-yl)propanamide (1.75 g, 3.5 mmol) in 30 mL 50% solution of acetonitrile in water was treated with 1.0 N HCl in water (3.85 mL, 3.85 mmol) and sonicated. The solution was frozen using a dry-ice acetone bath and then lyophilized to furnish (S)-2-(4-(2-chloro-5-cyano-3-((7-cyano-4-(ethylamino)imidazo[2,1-f][1,2,4]triazin-2-yl)amino)phenyl)piperazin-1-yl)propanamide, HCl (1.75 g, 90% yield)

LCMS (Phenomenex Luna C18 30×2 mm, 3u column, Solvent A=0.1% TFA in 90% water+10% acetonitrile; Solvent B=0.1% TFA in 10% water+90% acetonitrile, Flow rate 1.0 mL per minute, gradient 0-100% B over 2 min, followed by 1 minute at 100% B; Oven temperature: 40° C.); Detection: UV at 220 nm.

RT=1.7 min,

MS (ESI): m/z 494.5 (M+H)

1H NMR (400 MHz, DMSO-d6) δ 10.37 (br. s., 1H), 9.20 (t, J=5.7 Hz, 1H), 8.91 (s, 1H), 8.19 (s, 1H), 8.13 (s, 1H), 8.04 (d, J=1.5 Hz, 1H), 7.80 (s, 1H), 4.01 (d, J=6.4 Hz, 1H), 3.64-3.15 (m, 10H), 1.51 (d, J=6.8 Hz, 3H), 1.18 (t, J=7.2 Hz, 3H)

Example 2

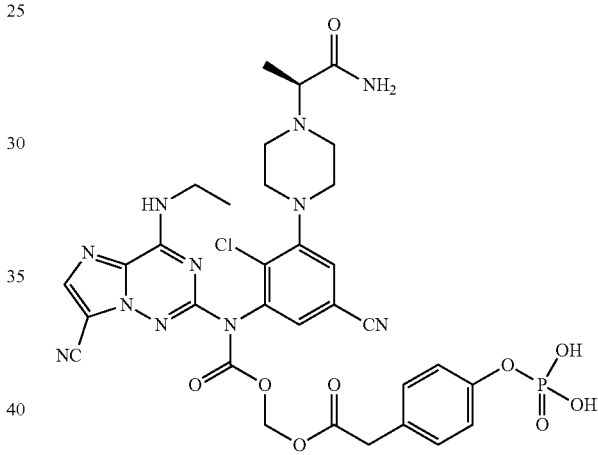

(S)-(((3-(4-(1-amino-1-oxopropan-2-yl)piperazin-1-yl)-2-chloro-5-cyanophenyl)(7-cyano-4-(ethylamino) imidazo[2,1-f][1,2,4]triazin-2-yl)carbamoyl)oxy) methyl 2-(4-(phosphonooxy)phenyl)acetate Step 1—Preparation of 2-chloro-4-(ethylamino) imidazo[2,1-f][1,2,4]triazine-7-carbonitrile (2A)

TFA (17.98 mL, 233 mmol) was added slowly to a solution of 2-chloro-4-(ethyl(4-methoxybenzyl)amino)imidazo[2,1-f][1,2,4]triazine-7-carbonitrile (intermediate 2) (8 g, 23.34 mmol) in dichloroethane (60 mL) and anisole (2.55 mL, 23.34 mmol). The reaction mixture was stirred at 55° C. for 1 h. The solvent was removed in vacuo and the material was azeotroped with toluene three times to remove the excess TFA. The crude was partitioned between ethyl acetate and 1.5 M potassium phosphate dibasic solution. The layers were separated and the aqueous layer was extracted with ethyl acetate two more times. The combined organic layers were dried over magnesium sulfate, filtered and concentrated in vacuo, 2-chloro-4-(ethylamino)imidazo[2,1-f][1,2,4]triazine-7-carbonitrile (5.2 g, 100% yield) was obtained as a white solid.

MS (ESI): m/z 223.1 (M+H)

$^1$H NMR (500 MHz, DMSO-d$_6$) δ 9.84 (br. s., 1H), 8.37 (s, 1H), 3.54 (q, J=7.2 Hz, 2H), 1.21 (t, J=7.1 Hz, 3H).

Step 2—Preparation of 4-(benzhydryl(ethyl)amino)-2-chloroimidazo[2,1-f][1,2,4]triazine-7-carbonitrile (2B)

A mixture of 2-chloro-4-(ethylamino)imidazo[2,1-f][1,2,4]triazine-7-carbonitrile (5.37 g, 24.12 mmol), (bromomethylene)dibenzene (14.30 g, 57.8 mmol) and cesium carbonate (20.69 g, 63.7 mmol) in DMF (60 mL) was stirred at room temperature for 24 hours. The solvent was evaporated and the residue was partitioned between ethyl acetate and 1.5 M potassium phosphate dibasic solution. The suspension in organic layer was collected by filtration to give 4.99 g of product. The layers were separated and the organic layer was washed with 1.5 M potassium phosphate dibasic solution, dried over magnesium sulfate, filtered and concentrated in vacuo, the crude product was purified by ISCO silica gel chromatography, eluting with 0-12% acetone/hexane to give 1.79 g of product. A total of 4-(benzhydryl(ethyl)amino)-2-chloroimidazo[2,1-f][1,2,4]triazine-7-carbonitrile (6.78 g, 72.3% yield) was obtained as a white solid.

MS (ESI): m/z 389.2 (M+H)

$^1$H NMR (400 MHz, chloroform-d) δ 8.91 (s, 0.58H), 8.04 (s, 0.32H), 7.96 (s, 0.56H), 7.73 (s, 0.34H), 7.45-7.35 (m, 6H), 7.30 (d, J=7.7 Hz, 4H), 4.38 (q, J=6.6 Hz, 0.74H), 3.91 (q, J=7.0 Hz, 1.23H), 0.72 (t, J=6.9 Hz, 3H) (mixture of rotamers in the ratio of 6 to 4)

Step 3—Preparation of tert-butyl 4-(3-((4-(benzhydryl(ethyl)amino)-7-cyanoimidazo[2,1-f][1,2,4]triazin-2-yl)amino)-2-chloro-5-cyanophenyl)piperazine-1-carboxylate (2C)

A mixture of 4-(benzhydryl(ethyl)amino)-2-chloroimidazo[2,1-f][1,2,4]triazine-7-carbonitrile (6.78 g, 17.44 mmol), tert-butyl 4-(3-amino-2-chloro-5-cyanophenyl)piperazine-1-carboxylate (intermediate 3) (5.87 g, 17.44 mmol), palladium(II) acetate (0.391 g, 1.744 mmol), DPPF (0.967 g, 1.744 mmol), xantphos (1.009 g, 1.744 mmol) and cesium carbonate (11.36 g, 34.9 mmol) in dioxane (80 mL) in a 100 mL flask was heated under nitrogen atmosphere at 75° C. for 3 h. The reaction mixture was diluted with dichloromethane and filtered through a bed of celite. The filtrate was concentrated and the crude product was purified by ISCO silica gel chromatography, eluting with 0-25% of 20% ethyl acetate in dichloromethane/dichloromethane to give tert-butyl 4-(3-((4-(benzhydryl(ethyl)amino)-7-cyanoimidazo[2,1-f][1,2,4]triazin-2-yl)amino)-2-chloro-5-cyanophenyl)piperazine-1-carboxylate (5.2 g, 43.3% yield).

MS (ESI): m/z 689.5 (M+H)

Step 4—Preparation of 4-(benzhydryl(ethyl)amino)-2-((2-chloro-5-cyano-3-(piperazin-1-yl)phenyl)amino) imidazo[2,1-f][1,2,4]triazine-7-carbonitrile (2D)

Trimethylsilyl trifluoromethanesulfonate (3.33 mL, 18.46 mmol) was added to a solution of tert-butyl 4-(3-((4-(benzhydryl(ethyl)amino)-7-cyanoimidazo[2,1-f][1,2,4]triazin-2-yl)amino)-2-chloro-5-cyanophenyl)piperazine-1-carboxylate (4.24 g, 6.15 mmol) and 2,6-lutidine (2.150 mL, 18.46 mmol) in DCM (10 mL) and the reaction mixture was stirred at room temperature for 1 hour. The reaction mixture was diluted with dichloromethane and washed with 1.5 M potassium phosphate dibasic solution three times. The organic layer was dried over magnessium sulfate, filtered and concentrated in vacuo, The crude product was purified by ISCO silica gel column chromatography eluting with 2-8% 2 N ammonia in methanol/dichloromethane. Fractions containing product were pooled and concentrated to give 4-(benzhydryl(ethyl)amino)-2-((2-chloro-5-cyano-3-(piperazin-1-yl)phenyl)amino) imidazo[2,1-f][1,2,4]triazine-7-carbonitrile (2.56 g, 70.6% yield) as a white solid.

MS (ESI): m/z 589.3 (M+H)

Step 5—Preparation of (S)-2-(4-(3-((4-(benzhydryl(ethyl)amino)-7-cyanoimidazo[2,1-f][1,2,4]triazin-2-yl)amino)-2-chloro-5-cyanophenyl)piperazin-1-yl) propanamide (2E)

Three parallel reactions in 0.4 g scale each were performed using the same conditions as below and combined for work up and purification:

A mixture of 4-(benzhydryl(ethyl)amino)-2-((2-chloro-5-cyano-3-(piperazin-1-yl)phenyl)amino)imidazo[2,1-f][1,2,4]triazine-7-carbonitrile (0.4 g, 0.679 mmol), (R)-1-amino-1-oxopropan-2-yl methanesulfonate (0.341 g, 2.037 mmol) and diisopropylamine (0.593 mL, 3.40 mmol) in acetonitrile (22.63 mL) in a sealed 40 mL vial was heated at 90° C. for 48 hours. The precipitate was collected by filtration to give 1.2 g of product. The filtrate was concentrated and purified by ISCO silica gel column chromatography eluting with 1.5-3.5% 2 N ammonia in methanol/dichloromethane to give 0.1 g of product. A total of 1.3 g of (S)-2-(4-(3-((4-(benzhydryl(ethyl)amino)-7-cyanoimidazo[2,1-f][1,2,4]triazin-2-yl)amino)-2-chloro-5-cyanophenyl)piperazin-1-yl)propanamide (97% yield) was obtained as an off-white solid.

MS (ESI): m/z 660.2 (M+H)

Step 6—Preparation of (S)-chloromethyl (3-(4-(1-amino-1-oxopropan-2-yl)piperazin-1-yl)-2-chloro-5-cyanophenyl)(4-(benzhydryl (ethyl)amino)-7-cyanoimidazo[2,1-f][1,2,4]triazin-2-yl)carbamate (2F)

Chloromethyl carbonochloridate (0.202 mL, 2.272 mmol) was added to a mixture of (S)-2-(4-(3-((4-(benzhydryl(ethyl)amino)-7-cyanoimidazo[2,1-f][1,2,4]triazin-2-yl)amino)-2-chloro-5-cyanophenyl)piperazin-1-yl)propanamide (0.5 g, 0.757 mmol), diisopropylamine (0.661 mL, 3.79 mmol) and DMAP (0.148 g, 1.212 mmol) in NMP (50.5 mL) and the reaction mixture was stirred at room temperature overnight. The reaction mixture was diluted with ethyl acetate and washed with half saturated sodium bicarbonate/ammonium chloride solution. The layers were separated and the aqueous layer was extracted with ethyl acetate two more times. The combined organic layers were washed with half saturated sodium bicarbonate/ammonium chloride solution twice and brine, dried over sodium sulfate, filtered and concentrated in vacuo to afford the crude (S)-chloromethyl (3-(4-(1-amino-1-oxopropan-2-yl)piperazin-1-yl)-2-chloro-5-cyanophenyl)(4-(benzhydryl (ethyl)amino)-7-cyanoimidazo[2,1-f][1,2,4]triazin-2-yl)carbamate, which was used as such in the next reaction.

MS (ESI): m/z 752.2 (M+H)

Step 7—Preparation of (S)-(((3-(4-(1-amino-1-oxopropan-2-yl)piperazin-1-yl)-2-chloro-5-cyanophenyl)(4-(benzhydryl(ethyl)amino)-7-cyanoimidazo[2,1-f][1,2,4]triazin-2-yl)carbamoyl)oxy)methyl 2-(4-((bis(benzyloxy)phosphoryl)oxy) phenyl)acetate (2G)

Cesium carbonate (0.216 g, 0.664 mmol) was added to a solution of (S)-chloromethyl (3-(4-(1-amino-1-oxopropan- 2-yl)piperazin-1-yl)-2-chloro-5-cyanophenyl)(4-(benzhydryl(ethyl)amino)-7-cyanoimidazo[2,1-f][1,2,4]triazin-2-yl)carbamate (0.5 g, 0.664 mmol) and 2-(4-((bis(benzyloxy)phosphoryl)oxy)phenyl)acetic acid (0.411 g, 0.996 mmol) in DMF (10 mL) and the reaction mixture was stirred at room temperature for 12 hours. The reaction mixture was diluted with ethyl acetate and washed with half saturated sodium bicarbonate/ammonium chloride solution. The layers were separated and the aqueous layer was extracted with ethyl acetate (2×). The combined organic layers were washed with half saturated sodium bicarbonate/ammonium chloride solution (2×) and brine, dried over sodium sulfate, filtered and concentrated in vacuo. The crude product was purified by ISCO silica gel column chromatography, eluting with 0.5-2.5% 2 N ammonia in methanol/dichloromethane) to give (S)-(((3-(4-(1-amino-1-oxopropan-2-yl)piperazin-1-yl)-2-chloro-5-cyanophenyl)(4-(benzhydryl(ethyl)amino)-7-cyanoimidazo[2,1-f][1,2,4]triazin-2-yl)carbamoyl)oxy)methyl 2-(4-((bis(benzyloxy)phosphoryl)oxy)phenyl)acetate (319 mg, 42.5% yield) as a colorless oil.

MS (ESI): m/z 1128.2 (M+H)

Step 8—Preparation of (S)-(((3-(4-(1-amino-1-oxopropan-2-yl)piperazin-1-yl)-2-chloro-5-cyanophenyl)(7-cyano-4-(ethylamino)imidazo[2,1-f][1,2,4]triazin-2-yl)carbamoyl)oxy)methyl 2-(4-((bis(benzyloxy)phosphoryl)oxy)phenyl)acetate (2H)

(S)-(((3-(4-(1-amino-1-oxopropan-2-yl)piperazin-1-yl)-2-chloro-5-cyanophenyl)(4-(benzhydryl(ethyl)amino)-7-cyanoimidazo[2,1-f][1,2,4]triazin-2-yl)carbamoyl)oxy)methyl 2-(4-((bis(benzyloxy)phosphoryl)oxy)phenyl)acetate (57 mg, 0.051 mmol) was treated with 10% TFA in DCM (1.7 mL, 2.020 mmol) at room temperature for 3 h. The reaction mixture was diluted with dichloromethane and washed with half saturated ammonium chloride/sodium bicarbonate solution. The layers were separated and the aqueous layer was extracted with dichloromethane (2×). The combined organic layers were dried over magnesium sulfate, filtered and concentrated in vacuo to give 48 mg of (S)-(((3-(4-(1-amino-1-oxopropan-2-yl)piperazin-1-yl)-2-chloro-5-cyanophenyl)(7-cyano-4-(ethylamino)imidazo[2,1-f][1,2,4]triazin-2-yl)carbamoyl)oxy)methyl 2-(4-((bis(benzyloxy)phosphoryl)oxy)phenyl)acetate (99% yield).

MS (ESI): m/z 962.3 (M+H)

Step 9—Preparation of Example 2

A mixture of (S)-(((3-(4-(1-amino-1-oxopropan-2-yl)piperazin-1-yl)-2-chloro-5-cyanophenyl)(7-cyano-4-(ethylamino)imidazo[2,1-f][1,2,4]triazin-2-yl)carbamoyl)oxy)methyl 2-(4-((bis(benzyloxy)phosphoryl)oxy)phenyl)acetate (48 mg, 0.050 mmol) and 10% Pd/C (10.62 mg, 9.98 µmol) in methanol (3 mL)/THF (1.5 mL) was hydrogenated with a balloon of hydrogen overnight. The reaction mixture was filtered through celite and the filtrate was concentrated in vacuo. The crude was purified by preparative HPLC (Phenomenex Luna Axia S5 C18 column, 21×250 mm, RT 7.065 min, 15-100% gradient aqueous acetonitrile over 15 minutes containing 5 mM ammonium acetate, 20 mL/min at 220 nm). Fractions containing product were combined and lyophilized to give (S)-(((3-(4-(1-amino-1-oxopropan-2-yl)piperazin-1-yl)-2-chloro-5-cyanophenyl)(7-cyano-4-(ethylamino)imidazo[2,1-f][1,2,4]triazin-2-yl)carbamoyl)oxy)methyl 2-(4-(phosphonooxy)phenyl)acetate (16.8 mg, 43.1% yield) was obtained as a white solid.

LCMS (Phenomenex Luna C18 30×2 mm, 3u column, Solvent A=0.1% TFA in 90% water+10% acetonitrile; Solvent B=0.1% TFA in 10% water+90% acetonitrile, Flow rate 1.0 mL per minute, gradient 0-100% B over 2 min, followed by 1 minute at 100% B; Oven temperature: 40° C.); Detection: UV at 220 nm.

RT=1.79 min

MS (ESI) m/z 782.1 (M+H)

$^1$H NMR (500 MHz, mixture of acetonitrile-$d_3$ and deuterium oxide) δ 8.06 (s, 1H), 7.47 (s, 2H), 7.19-7.10 (m, 5H), 5.88-5.59 (m, 2H), 3.68 (s, 2H), 3.35 (q, J=7.1 Hz, 3H), 2.95 (br. s., 4H), 1.39 (d, J=7.0 Hz, 3H), 1.06 (t, J=7.2 Hz, 3H)

$^{31}$P NMR (202 MHz, mixture of acetonitrile-$d_3$ and deuterium oxide) δ −4.9 (br. s., 1P)

Alternative Synthesis of Example 2

Step 1—Preparation of (S)-tert-butyl (2-((3-(4-(1-amino-1-oxopropan-2-yl)piperazin-1-yl)-2-chloro-5-cyanophenyl)(tert-butoxycarbonyl)amino)-7-cyanoimidazo[2,1-f][1,2,4]triazin-4-yl)(ethyl)carbamate (2A1)

(S)-2-(4-(2-chloro-5-cyano-3-((7-cyano-4-(ethylamino)imidazo[2,1-f][1,2,4]triazin-2-yl)amino)phenyl)piperazin-1-yl)propanamide, HCl salt (example 1, 115.7 mg, 0.218 mmol) was suspended in THF (8 mL) and acetonitrile (4 mL). DIPEA (0.25 mL, 1.431 mmol), BOC-anhydride (0.469 mL, 2.021 mmol) and DMAP (280 mg, 2.292 mmol) were added. The reaction mixture became a clear solution within 10 minutes. The reaction mixture was stirred at ambient temperature for 5 minutes beyond the complete dissolution. The reaction mixture was quenched by addition of NH$_3$/MeOH (2 molar solution, 10 mL, 20 mmol), stirred for 10 minutes and then partitioned between ethos and aqueous NH$_4$Cl solution. The organic layer was washed with brine, dried over MgSO$_4$, filtered and concentrated in vacuum to give 245 mg crude product as a yellow oil. The crude product was purified by ISCO silica gel column chromatography on silica (elution from 0% to 20% MeOH in DCM over 20 column volumes) to give (S)-tert-butyl (2-((3-(4-(1-amino-1-oxopropan-2-yl)piperazin-1-yl)-2-chloro-5-cyanophenyl)(tert-butoxycarbonyl)amino)-7-cyanoimidazo[2,1-f][1,2,4]triazin-4-yl)(ethyl)carbamate (0.11 g, 72.6% yield)

LCMS (Phenomenex Luna C18 30×2 mm, 3u column, Solvent A=0.1% TFA in 90% water+10% acetonitrile; Solvent B=0.1% TFA in 10% water+90% acetonitrile, Flow rate 1.0 mL per minute, gradient 0-100% B over 2 min, followed by 1 minute at 100% B; Oven temperature: 40° C.); Detection: UV at 220 nm.

RT=1.49 min

MS (ESI) m/z 694 and 696 (M+H)

1H NMR (400 MHz, CDCl$_3$) δ ppm 8.12 (s, 1H), 7.38 (d, J=1.7 Hz, 1H), 7.31 (d, J=1.7 Hz, 1H), 7.04 (d, J=4.5 Hz, 1H), 5.75 (d, J=3.8 Hz, 1H), 3.82 (q, J=7.0 Hz, 2H), 3.21-3.09 (m, 5H), 2.84-2.70 (m, 4H), 1.54 (s, 9H), 1.49 (s, 9H), 1.31 (d, J=7.0 Hz, 3H), 1.04 (t, J=6.9 Hz, 3H).

The structure was further confirmed by 2D NMR techniques (COSY, HMQC, HMBC, NOE).

Step 2—Preparation of (S)-tert-butyl (3-(4-(1-amino-1-oxopropan-2-yl)piperazin-1-yl)-2-chloro-5-cyanophenyl)(7-cyano-4-(ethylamino)imidazo[2,1-f][1,2,4]triazin-2-yl)carbamate (2A2)

(S)-tert-butyl (2-((3-(4-(1-amino-1-oxopropan-2-yl)piperazin-1-yl)-2-chloro-5-cyanophenyl)(tert-butoxycarbonyl)

amino)-7-cyanoimidazo[2,1-f][1,2,4]triazin-4-yl)(ethyl)carbamate (102 mg, 0.147 mmol) was dissolved in MeOH (6 mL). Ethylamine (70% solution in water) (0.6 mL, 7.55 mmol) was added. The mixture was stirred at ambient temperature for 45 minutes. The reaction mixture was partitioned between ethyl acetate and aqueous NaHCO$_3$ solution. The organic layer was washed with brine, dried over MgSO$_4$, filtered and evaporated to dryness to give 111 mg crude product (colorless film). The crude product was purified by ISCO silica gel column chromatography (gradient elution from 0% to 20% MeOH in DCM over 20 column volumes) to afford (S)-tert-butyl (3-(4-(1-amino-1-oxopropan-2-yl)piperazin-1-yl)-2-chloro-5-cyanophenyl)(7-cyano-4-(ethylamino)imidazo[2,1-f][1,2,4]triazin-2-yl)carbamate (80 mg, 68.5% yield).

LCMS (Phenomenex Luna C18 30×2 mm, 3u column, Solvent A=0.1% TFA in 90% water+10% acetonitrile; Solvent B=0.1% TFA in 10% water+90% acetonitrile, Flow rate 1.0 mL per minute, gradient 0-100% B over 2 min, followed by 1 minute at 100% B; Oven temperature: 40° C.); Detection: UV at 220 nm.

RT=1.24 min,

MS (ESI) m/z 594 and 596 (M+H)

1H NMR (400 MHz, CDCl$_3$) δ ppm 7.94 (s, 1H), 7.38 (d, J=1.7 Hz, 1H), 7.30 (d, J=1.7 Hz, 1H), 7.06 (br d, J~4 Hz, 1H), 6.63 (t, J=6 Hz, 1H), 5.37 (br d, J~4.4 Hz, 1H), 3.55-3.48 (m, 2H), 3.24-3.10 (m, 5H), 2.86-2.72 (m, 4H), 1.55 (s, 9H), 1.34 (d, J=7.1 Hz, 3H), 1.25 (t, J=7.2 Hz, 3H).

Step 3—Preparation of (S)-benzyl (2-((3-(4-(1-amino-1-oxopropan-2-yl)piperazin-1-yl)-2-chloro-5-cyanophenyl)(tert-butoxycarbonyl)amino)-7-cyanoimidazo[2,1-f][1,2,4]triazin-4-yl)(ethyl)carbamate (2A3)

(S)-tert-butyl (3-(4-(1-amino-1-oxopropan-2-yl)piperazin-1-yl)-2-chloro-5-cyanophenyl)(7-cyano-4-(ethylamino)imidazo[2,1-f][1,2,4]triazin-2-yl)carbamate (1.04 g, 1.523 mmol) was dissolved in THF (10 mL) and acetonitrile (5 mL). DMAP (0.279 g, 2.285 mmol) and DIPEA (1.596 mL, 9.14 mmol) were added. The mixture was cooled to 0° C. CBZ-Cl (0.544 mL, 3.81 mmol) was added dropwise. The reaction mixture was stirred at 0° C. for 4 hours, then stored in a −20° C. freezer overnight. Stirring was continued at 0° C. for 12 hr. DMAP (0.279 g, 2.285 mmol), DIPEA (1.596 mL, 9.14 mmol) and CBZ-Cl (0.544 mL, 3.81 mmol) were added. LCMS analysis of an aliquot 2 hours after the second reagent addition showed 5:1 ratio of product and starting material. Additional DMAP (0.141 g, 1.142 mmol), DIPEA (0.80 mL, 4.57 mmol) and CBZ-Cl (0.272 mL, 1.91 mmol) were added. Stirring at 0° C. was continued for 1 hour. The reaction mixture was partitioned between ethyl acetate and a mixture of dilute aqueous NH$_4$Cl and NaHCO$_3$ solution. The organic layer was washed two more times with NaHCO$_3$ and NH$_4$Cl solution (dilute), once with brine, then dried over MgSO$_4$, filtered and evaporated to dryness. The crude material was purified by ISCO silica gel column chromatography (gradient elution 0-15% Ethyl acetate in hexanes over 22 column volumes) to furnish (S)-benzyl (2-((3-(4-(1-amino-1-oxopropan-2-yl)piperazin-1-yl)-2-chloro-5-cyanophenyl)(tert-butoxycarbonyl)amino)-7-cyanoimidazo[2,1-f][1,2,4]triazin-4-yl)(ethyl)carbamate (1.57 g, 85% yield).

LCMS (Waters Aquity BEH C18 2.1×50 mm, 1.7 μm column, Solvent A=0.05% TFA in 100% water; Solvent B=0.05% TFA in 100% acetonitrile, Flow rate 0.8 mL per minute, gradient 2-98% B over 1.5 min, followed by 0.5 minutes at 98% B; Oven temperature: 40° C.); Detection: UV at 220 nm.

RT=1.14 min,

MS (ESI) m/z 728 and 730 (M+H)

1H NMR (400 MHz, CDCl$_3$) δ ppm 8.13 (s, 1H), 7.37-7.28 (m, 7H), 7.03 (br d, J~4.5 Hz, 1H), 5.42 (br d, J~4 Hz, 1H), 5.32 (s, 2H), 3.89 (q, J=7.0 Hz, 2H), 3.23-3.08 (m, 5H), 2.84-2.69 (m, 4H), 1.55 (s, 9H), 1.32 (d, J=7.0 Hz, 3H), 1.06 (t, J=7.0 Hz, 3H).

Step 4—Preparation of (S)-benzyl (2-((3-(4-(1-amino-1-oxopropan-2-yl)piperazin-1-yl)-2-chloro-5-cyanophenyl)amino)-7-cyanoimidazo[2,1-f][1,2,4]triazin-4-yl)(ethyl)carbamate (2A4)

To a solution of (S)-benzyl (2-((3-(4-(1-amino-1-oxopropan-2-yl)piperazin-1-yl)-2-chloro-5-cyanophenyl)(tert-butoxycarbonyl)amino)-7-cyanoimidazo[2,1-f][1,2,4]triazin-4-yl)(ethyl)carbamate (1.57 g, 1.294 mmol) in 1,2-dichloroethane (25 mL) was added anisole (7 mL, 64.1 mmol) followed by trifluoroacetic acid (7 mL, 91 mmol). The reaction mixture was stirred at room temperature. After a total reaction time of 2 hours the reaction mixture was evaporated to a sticky oil, which was partitioned between EtOAc and aqueous NaHCO$_3$ solution. The organic layer was washed with brine, dried over MgSO$_4$, filtered and evaporated to dryness. The crude was purified by column chromatography on silica. (24 g ISCO silica gel column, gradient elution 0-10% methanol in dichloromethane over 16 column volumes) to give (S)-benzyl (2-((3-(4-(1-amino-1-oxopropan-2-yl)piperazin-1-yl)-2-chloro-5-cyanophenyl)amino)-7-cyanoimidazo[2,1-f][1,2,4]triazin-4-yl)(ethyl)carbamate (0.69 g, 81% yield).

LCMS (Phenomenex Luna C18 30×2 mm, 3u column, Solvent A=0.1% TFA in 90% water+10% acetonitrile; Solvent B=0.1% TFA in 10% water+90% acetonitrile, Flow rate 1.0 mL per minute, gradient 0-100% B over 2 min, followed by 1 minute at 100% B; Oven temperature: 40° C.); Detection: UV at 220 nm.

RT=1.36 min

MS (ESI) m/z 628 and 630 (M+H)

1H NMR (400 MHz, CDCl$_3$) δ ppm 8.53 (d, J=1.8 Hz, 1H), 8.07 (s, 1H), 7.64 (s, 1H), 7.40-7.32 (m, 5H), 7.09 (d, J=1.7 Hz, 1H), 7.05 (br d, J~4 Hz, 1H), 5.37 (br, 3H), 4.21 (q, J=7.0 Hz, 2H), 3.22 (q, J=7.0 Hz, 1H), 3.18-3.07 (m, 4H), 2.87-2.73 (m, 4H), 1.41 (t, J=7.0 Hz, 3H), 1.35 (d, J=7.0 Hz, 3H).

Step 5—Preparation of (S)-benzyl (2-((3-(4-(1-amino-1-oxopropan-2-yl)piperazin-1-yl)-2-chloro-5-cyanophenyl)((chloromethoxy)carbonyl)amino)-7-cyanoimidazo[2,1-f][1,2,4]triazin-4-yl)(ethyl)carbamate (2A5)

(S)-benzyl (2-((3-(4-(1-amino-1-oxopropan-2-yl)piperazin-1-yl)-2-chloro-5-cyanophenyl)amino)-7-cyanoimidazo[2,1-f][1,2,4]triazin-4-yl)(ethyl)carbamate (300 mg, 0.454 mmol) and DMAP (72.1 mg, 0.590 mmol) were dissolved in N-methyl-2-pyrrolidinone (4.5 mL). The solution was cooled to 0° C. DIPEA (476 μl, 2.72 mmol) was added, followed by chloromethyl carbonochloridate (81 μl, 0.908 mmol). The reaction mixture was stirred at 0° C. for 90 minutes, then partitioned between EtOAc and dilute aqueous NaHCO$_3$ solution. The organic layer was extracted 3× with dilute NH$_4$Cl and NaHCO$_3$ solution, once with brine, then dried over MgSO$_4$, filtered and evaporated to dryness to give (S)-benzyl (2-((3-(4-(1-amino-1-oxopropan-2-yl)piperazin-1-yl)-2-chloro-5-cyanophenyl)((chloromethoxy)carbonyl)amino)-7-cyanoimidazo[2,1-f][1,2,4]triazin-4-yl)(ethyl)carbamate (355.7 mg, 92% yield). The product was used as such in the next reaction without further purification.

LCMS (Phenomenex Luna C18 30×2 mm, 3u column, Solvent A=0.1% TFA in 90% water+10% acetonitrile; Solvent B=0.1% TFA in 10% water+90% acetonitrile, Flow rate 1.0 mL per minute, gradient 0-100% B over 2 min, followed by 1 minute at 100% B; Oven temperature: 40° C.); Detection: UV at 220 nm.

RT=1.40 min

MS (ESI) m/z 720/722/724 (M+H)

1H NMR (600 MHz, dmso-d6) δ ppm 8.61 (s, 1H), 7.81 (d, J 1.2 Hz, 1H), 7.70 (d, J=1.2 Hz, 1H), 7.36-7.29 (m, 5H), 7.25 (br s, 1H), 7.03 (br s, 1H), 6.07-5.94 (br, 2H), 5.26 (s, 2H), 3.82-3.77 (br, 2H), 3.12-3.04 (m, 5H), 2.71-2.61 (m, 4H), 1.14 (d, J=7.0 Hz, 3H), 0.98 (t, J=7.0 Hz, 3H).

Step 6—Preparation of (S)-(((3-(4-(1-amino-1-oxopropan-2-yl)piperazin-1-yl)-2-chloro-5-cyanophenyl)(4-(((benzyloxy)carbonyl)(ethyl)amino)-7-cyanoimidazo[2,1-f][1,2,4]triazin-2-yl)carbamoyl)oxy)methyl 2-(4-((bis(benzyloxy)phosphoryl)oxy)phenyl)acetate (2A6)

(S)-benzyl (2-((3-(4-(1-amino-1-oxopropan-2-yl)piperazin-1-yl)-2-chloro-5-cyanophenyl)((chloromethoxy)carbonyl)amino)-7-cyanoimidazo[2,1-f][1,2,4]triazin-4-yl)(ethyl)carbamate (66 mg, 0.060 mmol), Cs₂CO₃ (25.2 mg, 0.077 mmol) and 2-(4-((bis(benzyloxy)phosphoryl)oxy)phenyl)acetic acid (36.8 mg, 0.089 mmol), (prepared according to procedure in WO2012135082) were combined/dissolved in DMF (0.5 mL) and stirred at ambient temperature for 24 hours. The reaction mixture was filtered, solids rinsed with DMF and the filtrate purified by preparative HPLC. (XBridge C18 5u OBD 19×100 mm column, water/CH₃CN gradient with 10 mM NH₄OAc). Product containing fractions were evaporated to dryness (under a nitrogen stream overnight) to give (S)-(((3-(4-(1-amino-1-oxopropan-2-yl)piperazin-1-yl)-2-chloro-5-cyanophenyl)(4-(((benzyloxy)carbonyl)(ethyl)amino)-7-cyanoimidazo[2,1-f][1,2,4]triazin-2-yl)carbamoyl)oxy)methyl 2-(4-((bis(benzyloxy)phosphoryl)oxy)phenyl)acetate (34.8 mg 53.3% yield).

LCMS (Phenomenex Luna C18 30×2 mm, 3u column, Solvent A=0.1% TFA in 90% water+10% acetonitrile; Solvent B=0.1% TFA in 10% water+90% acetonitrile, Flow rate 1.0 mL per minute, gradient 0-100% B over 2 min, followed by 1 minute at 100% B; Oven temperature: 40° C.); Detection: UV at 220 nm.

Rt=1.72 min

MS (ESI) m/z 1096/1098 (M+H)

Step 6—Preparation of Example 2

A round bottom flask was loaded with (S)-(((3-(4-(1-amino-1-oxopropan-2-yl)piperazin-1-yl)-2-chloro-5-cyanophenyl)(4-(((benzyloxy)carbonyl)(ethyl)amino)-7-cyanoimidazo[2,1-f][1,2,4]triazin-2-yl)carbamoyl)oxy)methyl 2-(4-((bis(benzyloxy)phosphoryl)oxy)phenyl)acetate (18 mg, 0.016 mmol) and 10% Pd—C (6.5 mg, 6.11 μmol). Methanol (6 mL) and THF (2 mL) were added. Hydrogen was bubbled through the reaction mixture with vigorous stirring for 4 hours. The reaction mixture was filtered through a 0.45 μm Nylon filter and evaporated to dryness (water bath temp <30° C.). The crude material was dissolved in DMSO and purified by preparative HPLC (water/CH₃CN gradient, 10 mM NH₄OAc, XBridge C18 5u OBD 19×100 mm column). Product containing fractions were combined, frozen and lyophilized to dryness. (S)-(((3-(4-(1-amino-1-oxopropan-2-yl)piperazin-1-yl)-2-chloro-5-cyanophenyl)(7-cyano-4-(ethylamino)imidazo[2,1-f][1,2,4]triazin-2-yl)carbamoyl)oxy)methyl 2-(4-(phosphonooxy)phenyl)acetate (4.9 mg, 34.3% yield).

LCMS (Phenomenex Luna C18 50×2 mm, 3u column, Solvent A=0.1% TFA in 90% water+10% acetonitrile; Solvent B=0.1% TFA in 10% water+90% acetonitrile, Flow rate 1.0 mL per minute, gradient 0-100% B over 4 min, followed by 1 minute at 100% B; Oven temperature: 40° C.); Detection: UV at 220 nm.

RT=1.83 min

MS (ESI) m/z 781 (M+H)

1H NMR (400 MHz, D₂O) δ ppm 7.98 (s, 1H), 7.57 (s, 1H), 7.48 (s, 1H), 7.10 (d, J=8.3 Hz, 2H), 7.04 (d, J=8.0 Hz, 2H), 5.82-5.56 (br, 2H), 3.65 (s, 2H), 3.29-3.15 (m, 3H), 3.07-2.85 (m, 4H), 2.78-2.61 (m, 4H), 1.25 (d, J=6.6 Hz, 3H), 0.86 (t, J=7.2 Hz, 3H).

Example 3

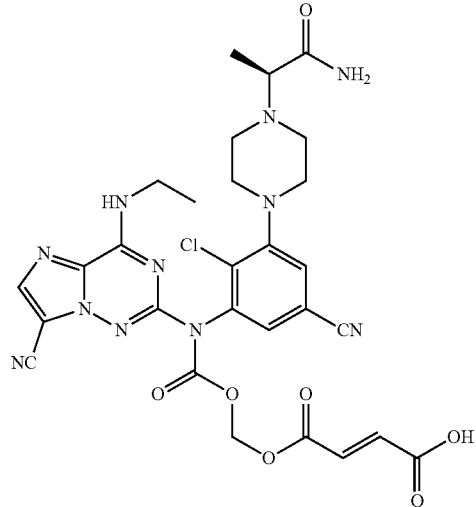 [SMILES: CCNc1nc(N(C(=O)OCOC(=O)/C=C/C(=O)O)c2cc(C#N)cc(N3CCN([C@@H](C)C(N)=O)CC3)c2Cl)nn2c(C#N)cnc12]

(S,E)-4-((((3-(4-(1-amino-1-oxopropan-2-yl)piperazin-1-yl)-2-chloro-5-cyanophenyl)(7-cyano-4-(ethylamino)imidazo[2,1-f][1,2,4]triazin-2-yl)carbamoyl)oxy)methoxy)-4-oxobut-2-enoic Acid Step 1—Preparation of (S,E)-4-((((3-(4-(1-amino-1-oxopropan-2-yl)piperazin-1-yl)-2-chloro-5-cyanophenyl)(4-(benzhydryl(ethyl)amino)-7-cyanoimidazo[2,1-f][1,2,4]triazin-2-yl)carbamoyl)oxy)methoxy)-4-oxobut-2-enoic acid (3A)

Tetrabutylammonium (E)-3-carboxyacrylate (213 mg, 0.595 mmol), prepared by freeze-drying an aqueous solution of equimolar tetrabutylammonium hydroxide (40% aqueous solution) and fumaric acid, was added to a solution of (S)-chloromethyl (3-(4-(1-amino-1-oxopropan-2-yl)piperazin-1-yl)-2-chloro-5-cyanophenyl)(4-(benzhydryl(ethyl)amino)-7-cyanoimidazo[2,1-f][1,2,4]triazin-2-yl)carbamate (example 2F) (55.7 mg, 0.074 mmol) in DMF (0.5 mL) and the reaction mixture was stirred at room temperature for 3 hours. The reaction mixture was diluted with methanol and purified by preparative HPLC (Phenomenex Axia 5u C18 column, 21×50 mm, RT 10.281 min, 30-100% gradient aqueous acetonitrile over 15 minutes containing 0.05% TFA, 20 mL/min at 220 nm). Fractions containing product were concentrated to give (S,E)-4-((((3-(4-(1-amino-1-oxopropan-2-yl)piperazin-1-yl)-2-chloro-5-cyanophenyl)(4-(benzhydryl(ethyl)amino)-7-cyanoimidazo[2,1-f][1,2,4]triazin-2-yl)carbamoyl)oxy)methoxy)-4-oxobut-2-enoic acid (50 mg, 81% yield) as a white solid.

MS (ESI) m/z 832.2 (M+H)

Step 2—Preparation of Example 3

(S,E)-4-((((3-(4-(1-amino-1-oxopropan-2-yl)piperazin-1-yl)-2-chloro-5-cyanophenyl)(4-(benzhydryl(ethyl)amino)-7-cyanoimidazo[2,1-f][1,2,4]triazin-2-yl)carbamoyl)oxy)methoxy)-4-oxobut-2-enoic acid (63 mg, 0.076 mmol) was treated with 10% TFA in DCM (3.5 ml, 3.78 mmol) and the reaction mixture was stirred at room temperature for 1.5 hours. triethylamine (528 μl, 3.78 mmol) was added to neutralize the acid and the reaction solution was diluted with methanol and the crude was purified by preparative HPLC (Phenomenex Luna Axia S5 C18 column, 21×250 mm, RT 8.374 min, 10-100% gradient aqueous acetonitrile over 15 minutes containing 5 mM ammonium acetate, 20 mL/min at 220 nm). (S,E)-4-((((3-(4-(1-amino-1-oxopropan-2-yl)piperazin-1-yl)-2-chloro-5-cyanophenyl)(7-cyano-4-(ethylamino)imidazo[2,1-f][1,2,4]triazin-2-yl)carbamoyl)oxy)methoxy)-4-oxobut-2-enoic acid (30 mg, 59.5% yield) was obtained as a white solid.

LCMS (Phenomenex Luna C18 30×2 mm, 3u column, Solvent A=0.1% TFA in 90% water+10% acetonitrile; Solvent B=0.1% TFA in 10% water+90% acetonitrile, Flow rate 1.0 mL per minute, gradient 0-100% B over 2 min, followed by 1 minute at 100% B; Oven temperature: 40° C.); Detection: UV at 220 nm.

RT=1.62 min

MS (ESI): m/z 666.1 (M+H)

$^1$H NMR (500 MHz, deuterium oxide) δ 7.88 (br. s., 1H), 7.61 (d, J=15.7 Hz, 2H), 6.85 (dd, J=15.8, 2.5 Hz, 1H), 6.43-6.31 (m, 1H), 5.77 (br. s., 2H), 3.77 (br. s., 1H), 3.48-3.03 (m, 10H), 1.50 (d, J=6.0 Hz, 3H), 0.95 (t, J=6.2 Hz, 3H)

Example 4

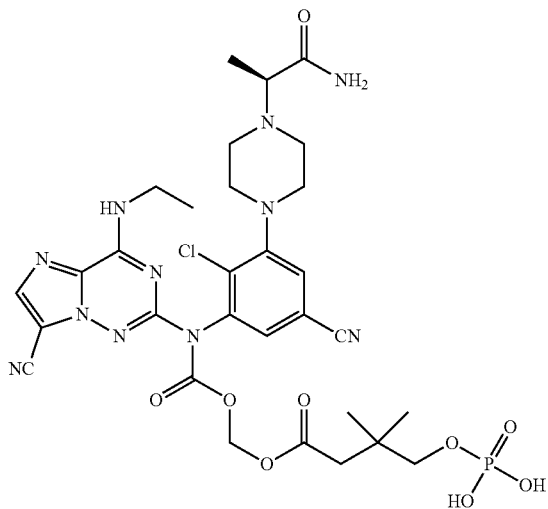 [SMILES: CCNc1nc(N(C(=O)OCOC(=O)CC(C)(C)COP(=O)(O)O)c2cc(C#N)cc(N3CCN([C@@H](C)C(N)=O)CC3)c2Cl)nn2c(C#N)cnc12]

(S)-(((3-(4-(1-amino-1-oxopropan-2-yl)piperazin-1-yl)-2-chloro-5-cyanophenyl)(7-cyano-4-(ethylamino)imidazo[2,1-f][1,2,4]triazin-2-yl)carbamoyl)oxy) methyl 3,3-dimethyl-4-(phosphonooxy)butanoate Step 1—Preparation of (S)-(((3-(4-(1-amino-1-oxopropan-2-yl)piperazin-1-yl)-2-chloro-5-cyanophenyl)(4-(benzhydryl(ethyl)amino)-7-cyanoimidazo[2,1-f][1,2,4]triazin-2-yl)carbamoyl)oxy)methyl 4-((di-tert-butoxyphosphoryl)oxy)-3,3-dimethylbutanoate (4A)

Cesium carbonate (43.3 mg, 0.133 mmol) was added to a solution of (S)-chloromethyl (3-(4-(1-amino-1-oxopropan-2-yl)piperazin-1-yl)-2-chloro-5-cyanophenyl)(4-(benzhydryl(ethyl)amino)-7-cyanoimidazo[2,1-f][1,2,4]triazin-2-yl)carbamate (example 2F) (100 mg, 0.133 mmol) and 4-((di-tert-butoxyphosphoryl)oxy)-3,3-dimethylbutanoic acid (prepared according to procedure: Degoey WO 2006/014282) (43.1 mg, 0.133 mmol) in DMF (3 mL) and the reaction mixture was stirred at room temperature for 12 hours. The reaction mixture was diluted with dichloromethane and washed with half saturated ammonium chloride/sodium bicarbonate solution. The layers were separated and the aqueous layer was extracted with dichloromethane two more times. The combined organic layers were dried over magnessium sulfate, filtered and concentrated in vacuo. The crude product was purified by flash chromatography on silica gel using ISCO silica gel column chromatography (gradient elution with 0.5-5% 2 N ammonia in methanol/dichloromethane). (S)-(((3-(4-(1-amino-1-oxopropan-2-yl)piperazin-1-yl)-2-chloro-5-cyanophenyl)(4-(benzhydryl(ethyl)amino)-7-cyanoimidazo[2,1-f][1,2,4]triazin-2-yl)carbamoyl)oxy)methyl 4-((di-tert-butoxyphosphoryl)oxy)-3,3-dimethylbutanoate (46 mg, 0.044 mmol, 33.3% yield) as a colorless oil.

MS (ESI) m/z 1040.1 (M+H)

Step 2—Preparation of Example 4

(S)-(((3-(4-(1-amino-1-oxopropan-2-yl)piperazin-1-yl)-2-chloro-5-cyanophenyl)(4-(benzhydryl(ethyl)amino)-7-cyanoimidazo[2,1-f][1,2,4]triazin-2-yl)carbamoyl)oxy)methyl 4-((di-tert-butoxyphosphoryl)oxy)-3,3-dimethylbutanoate (46 mg, 0.044 mmol) was treated with 10% TFA in DCM (1.9 mL, 2.210 mmol) at room temperature for 1 h. The reaction mixture was cooled to 0° C. and quenched with slow addition of triethylamine (308 μl, 2.210 mmol). The solvent was evaporated in vacuo and the crude was purified by preparative HPLC (Phenomenex Gemini C18 column, 5 μm, 21×250 mm, RT 7.889 min, 10-100% gradient aqueous acetonitrile over 12 minutes containing 5 mM ammonium acetate, 20 mL/min at 260 nm). Fractions containing product were combined and lyophilized to give (S)-(((3-(4-(1-amino-1-oxopropan-2-yl)piperazin-1-yl)-2-chloro-5-cyanophenyl)(7-cyano-4-(ethylamino)imidazo[2,1-f][1,2,4]triazin-2-yl)carbamoyl)oxy)methyl 3,3-dimethyl-4-(phosphonooxy)butanoate (12 mg, 0.015 mmol, 34.5% yield) as a white solid.

LCMS (Phenomenex Luna C18 30×2 mm, 3u column, Solvent A=0.1% TFA in 90% water+10% acetonitrile; Solvent B=0.1% TFA in 10% water+90% acetonitrile, Flow rate 1.0 mL per minute, gradient 0-100% B over 2 min, followed by 1 minute at 100% B; Oven temperature: 40° C.); Detection: UV at 220 nm.

RT=1.75 min

MS (ESI) m/z 762.0 (M+H)

¹H NMR (500 MHz, mixture of acetonitrile-d₃ and deuterium oxide) δ 8.06 (s, 1H), 7.51 (s, 2H), 5.76 (br. s., 2H), 3.50 (d, J=4.4 Hz, 2H), 3.40-3.33 (m, 2H), 3.18-3.06 (m, 5H), 2.81-2.64 (m, 4H), 2.34 (s, 2H), 1.23 (d, J=7.0 Hz, 3H), 1.07 (t, J=7.2 Hz, 3H), 0.94 (s, 6H)

Example 5

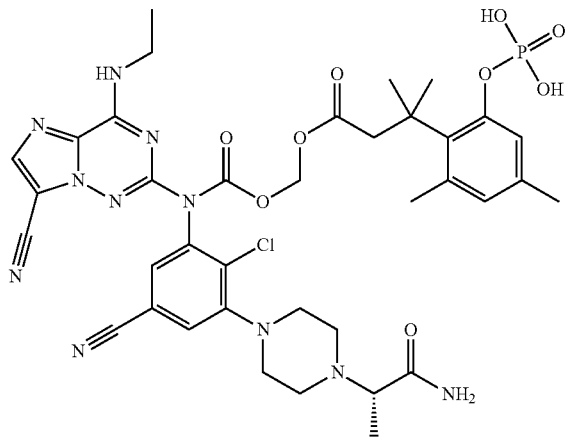 [SMILES: CCNc1nc(N(C(=O)OCOC(=O)CC(C)(C)c2c(C)cc(C)cc2OP(=O)(O)O)c2cc(C#N)cc(N3CCN([C@@H](C)C(N)=O)CC3)c2Cl)nn2c(C#N)cnc12]

(S)-(((3-(4-(1-amino-1-oxopropan-2-yl)piperazin-1-yl)-2-chloro-5-cyanophenyl)(7-cyano-4-(ethylamino)imidazo[2,1-f][1,2,4]triazin-2-yl)carbamoyl)oxy)methyl 3-(2,4-dimethyl-6-(phosphonooxy)phenyl)-3-methylbutanoate Step 1—Preparation of (S)-(((3-(4-(1-amino-1-oxopropan-2-yl)piperazin-1-yl)-2-chloro-5-cyanophenyl)(4-(((benzyloxy)carbonyl)(ethyl)amino)-7-cyanoimidazo[2,1-f][1,2,4]triazin-2-yl)carbamoyl)oxy)methyl 3-(2-((bis(benzyloxy)phosphoryl)oxy)-4,6-dimethylphenyl)-3-methylbutanoate (5A)

(S)-benzyl (2-((3-(4-(1-amino-1-oxopropan-2-yl)piperazin-1-yl)-2-chloro-5-cyanophenyl)((chloromethoxy)carbonyl)amino)-7-cyanoimidazo[2,1-f][1,2,4]triazin-4-yl)(ethyl)carbamate (example 2A5) (170 mg, 0.201 mmol), Cs₂CO₃ (85 mg, 0.261 mmol) and 3-(2-((bis(benzyloxy)phosphoryl)oxy)-4,6-dimethylphenyl)-3-methylbutanoic acid (207 mg, 0.301 mmol) (prepared according to WO 2007076034) were dissolved in DMF (3 mL) and stirred at ambient temperature for 3 days. The reaction mixture was partitioned between EtOAc and dilute aqueous NaHCO₃ solution. The aqueous layer was extracted one more time with EtOAc. The organic layers were washed twice with dilute aqueous NaHCO₃ solution, then once with brine. The combined organic layers were dried over MgSO₄, filtered and evaporated to dryness. The crude product was purified using ISCO silica gel column chromatography (gradient elution from 0 to 50% EtOAc in DCM over 30 column volumes) to give (S)-(((3-(4-(1-amino-1-oxopropan-2-yl)piperazin-1-yl)-2-chloro-5-cyanophenyl)(4-(((benzyloxy)carbonyl)(ethyl)amino)-7-cyanoimidazo[2,1-]][1,2,4]triazin-2-yl)carbamoyl)oxy)methyl 3-(2-((bis(benzyloxy)phosphoryl)oxy)-4,6-dimethylphenyl)-3-methylbutanoate (0.20 g, 47.0% yield).

LCMS (Phenomenex Luna C18 30×2 mm, 3u column, Solvent A=0.1% TFA in 90% water+10% acetonitrile; Solvent B=0.1% TFA in 10% water+90% acetonitrile, Flow rate 1.0 mL per minute, gradient 0-100% B over 2 min, followed by 1 minute at 100% B; Oven temperature: 40° C.); Detection: UV at 220 nm.

RT=1.82 min

MS (ESI) m/z 1166/1168 (M+H)

1H NMR (500 MHz, CDCl₃) δ ppm 8.17 (s, 1H), 7.95-7.70 (br, 1H), 7.42 (s, 1H), 7.38-7.27 (m, 16H), 6.99 (s, 1H), 6.75 (s, 1H), 6.30-6.05 (br, 1H), 5.64 (s, 2H), 5.35 (s, 2H), 5.17-5.09 (m, 4H), 4.5-4.2 (very broad, 1H), 4.00 (q, J=7 Hz, 2H), 3.80-3.65 (br, 2H), 3.54-3.32 (m, 6H), 2.95 (br, 2H), 2.49 (s, 3H), 2.16 (s, 3H), 1.69-1.60 (br, 3H), 1.57 (s, 3H), 1.56 (s, 3H), 1.16 (t, J=7 Hz, 3H).

31P NMR (202 MHz, CDCl₃) δ ppm −9.12 (pent, J~8 Hz)

Step 2—Preparation of Example 5

A round bottom flask was loaded with (S)-(((3-(4-(1-amino-1-oxopropan-2-yl)piperazin-1-yl)-2-chloro-5-cyanophenyl)(4-(((benzyloxy)carbonyl)(ethyl) amino)-7-cyanoimidazo[2,1-f][1,2,4]triazin-2-yl)carbamoyl)oxy)methyl 3-(2-((bis(benzyloxy)phosphoryl)oxy)-4,6-dimethylphenyl)-3-methylbutanoate (43 mg, 0.026 mmol) and 20% Pd(OH)₂ on carbon (16 mg, 0.011 mmol). Methanol (9 mL) and THF (3 mL) were added. Hydrogen was bubbled through the mixture with vigorous stirring for 1.5 hours. After 1.5 hours the reaction flask was flushed with nitrogen. The mixture was filtered through a 0.45 μm Nylon filter and evaporated to dryness (water bath temp <28° C.). The material was dissolved in DMSO and purified by preparative HPLC (water/CH₃CN gradient, 0.1% TFA, Sunfire C18 5u OBD 19×100 mm column). Product containing fractions were combined, frozen and lyophilized to afford (S)-(((3-(4-(1-amino-1-oxopropan-2-yl)piperazin-1-yl)-2-chloro-5-cyanophenyl)(7-cyano-4-(ethylamino)imidazo[2,1-f][1,2,4]triazin-2-yl)carbamoyl)oxy)methyl 3-(2,4-dimethyl-6-(phosphonooxy)phenyl)-3-methylbutanoate (9.0 mg, 40.1% yield).

LCMS (Phenomenex Luna C18 30×2 mm, 3u column, Solvent A=0.1% TFA in 90% water+10% acetonitrile; Solvent B=0.1% TFA in 10% water+90% acetonitrile, Flow rate 1.0 mL per minute, gradient 0-100% B over 2 min, followed by 1 minute at 100% B; Oven temperature: 40° C.); Detection: UV at 220 nm.

RT=1.20 min,

MS (ESI) m/z 852/854 (M+H)

1H NMR (500 MHz, dmso-d6) δ ppm 9.57 (t, J=5.9 Hz, 1H), 8.37 (s, 1H), 7.68 (d, J=1.9 Hz, 1H), 7.62 (d, J=1.9 Hz, 1H), 7.45-7.38 (br, 1H), 7.15 (br, 1H), 7.09 (br, 1H), 6.53 (br, 1H), 5.64 (br s, 2H), 2.78-2.66 (m, 4H), 2.65 (p, J=1.9 Hz, 1H), 2.39 (s, 3H), 2.37 (p, J=1.9 Hz, 1H), 2.13 (s, 3H), 1.49 (s, 6H), 1.16 (d, J=6.8 Hz, 3H), 0.99 (t, J=7.1 Hz, 3H). 7 proton signals are obscured by the large water and dmso signals.

31P NMR (202 MHz, dmso-d6) δ ppm −7.1 (s)

What is claimed is:

1. A compound having Formula (I)

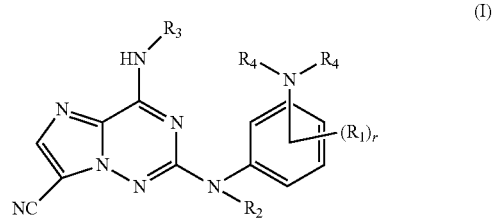

or a stereoisomer, a tautomer, a pharmaceutically acceptable salt thereof, wherein
  $R_1$ is H, Cl, or CN;
  $R_2$ is —C(=O)O(CR$_c$R$_c$)$_r$OC(=O)R$_d$;
  $R_3$ is ethyl or cyclopropyl;
  $R_4$ and $R_4$ together with the nitrogen atom to which they are both attached form

$R_5$ is —CHR$_c$C(=O)NH$_2$;
  $R_6$ is H;
  $R_c$ is H or $C_{1-6}$ alkyl;
  $R_d$ is

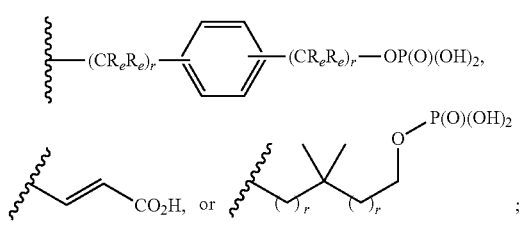

$R_e$ is H or $C_{1-4}$ alkyl; and
  r is zero, 1, 2 or 3.

2. The compound of claim 1 or a stereoisomer, a tautomer, a pharmaceutically acceptable salt thereof, wherein
  $R_1$ is H, Cl, or CN;
  $R_2$ is —C(=O)OCH$_2$OC(=O)R$_d$;
  $R_3$ is ethyl;
  $R_4$ and $R_4$ together with the nitrogen atom to which they are both attached form

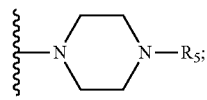

$R_5$ is —CH(CH$_3$)C(=O)NH$_2$;
  $R_d$ is

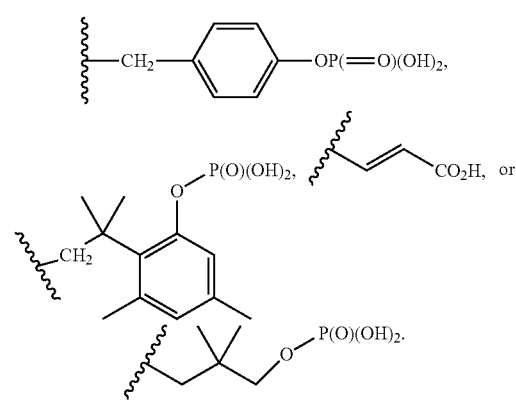

3. The compound of claim 2 selected from the group consisting of

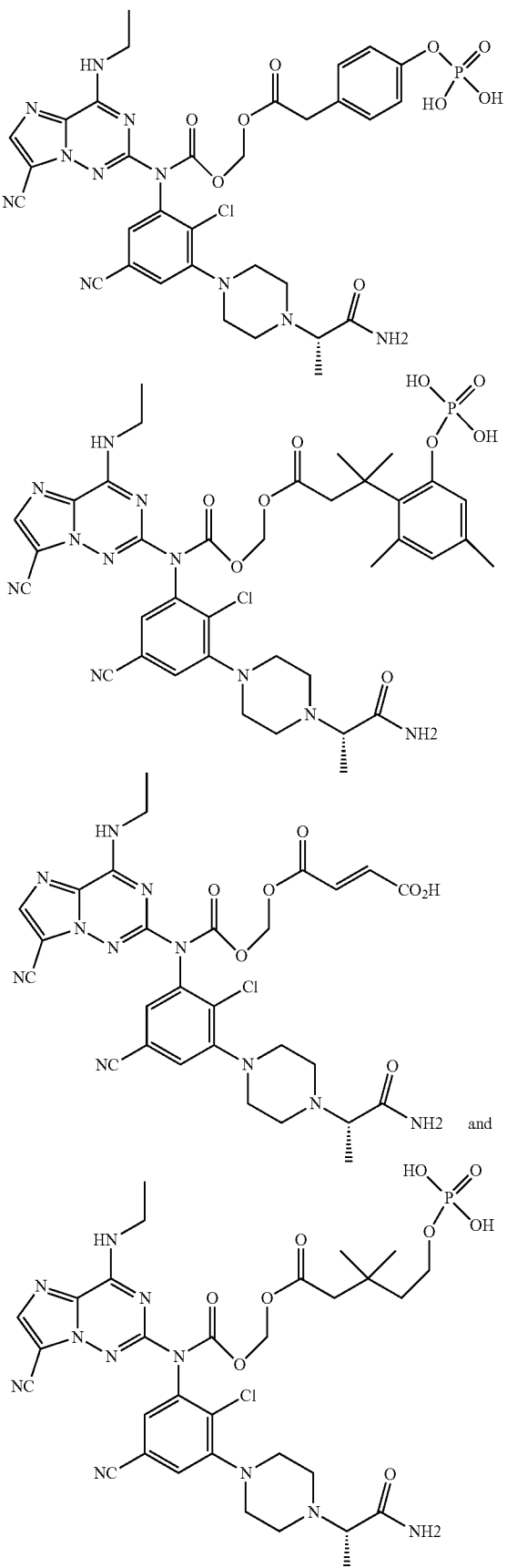

and or a stereoisomer, a tautomer, a pharmaceutically acceptable salt thereof.
4. The compound having the structure
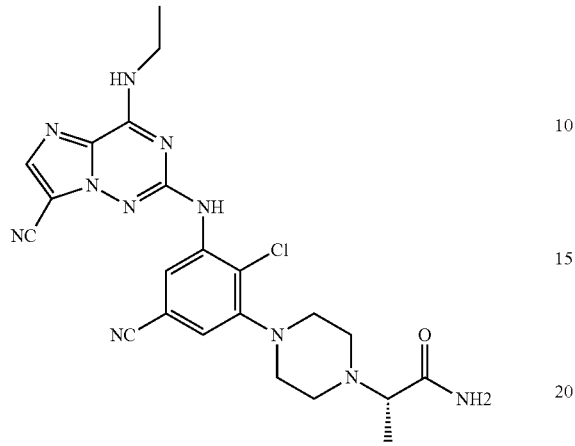
or a stereoisomer, a tautomer, a pharmaceutically acceptable salt thereof.
5. A pharmaceutical composition comprising one or more compounds according to claim 1 and a pharmaceutically acceptable carrier.
* * * * *